US009919981B2

(12) United States Patent
Chojecki et al.

(10) Patent No.: US 9,919,981 B2
(45) Date of Patent: Mar. 20, 2018

(54) CONVERSION OF CARBON MONOXIDE, CARBON DIOXIDE, OR A COMBINATION THEREOF OVER HYBRID CATALYST

(71) Applicant: Dow Global Technologies LLC, Midland, MI (US)

(72) Inventors: Adam Chojecki, Terneuzen (NL); Davy Nieskens, Terneuzen (NL); Thomas Davidian, Terneuzen (NL); Peter E. Groenendijk, Hulst (NL); Matthijs Ruitenbeek, Terneuzen (NL); Barry B. Fish, Freeport, TX (US); Max M. Tirtowidjojo, Freeport, TX (US); Garmt R. Meima, Terneuzen (NL)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/324,869

(22) PCT Filed: Jul. 8, 2015

(86) PCT No.: PCT/US2015/039522
§ 371 (c)(1),
(2) Date: Jan. 9, 2017

(87) PCT Pub. No.: WO2016/007607
PCT Pub. Date: Jan. 14, 2016

(65) Prior Publication Data
US 2017/0210679 A1    Jul. 27, 2017

Related U.S. Application Data

(60) Provisional application No. 62/023,500, filed on Jul. 11, 2014.

(51) Int. Cl.
| C07C 1/04 | (2006.01) |
| C07C 1/12 | (2006.01) |
| B01J 37/03 | (2006.01) |
| B01J 37/04 | (2006.01) |
| B01J 35/02 | (2006.01) |
| B01J 35/00 | (2006.01) |
| B01J 23/26 | (2006.01) |
| B01J 29/85 | (2006.01) |
| B01J 23/80 | (2006.01) |

(52) U.S. Cl.
CPC ............. *C07C 1/043* (2013.01); *B01J 23/26* (2013.01); *B01J 23/80* (2013.01); *B01J 29/85* (2013.01); *B01J 35/0006* (2013.01); *B01J 35/026* (2013.01); *B01J 37/031* (2013.01); *B01J 37/04* (2013.01); *C07C 1/12* (2013.01); *C07C 2521/04* (2013.01); *C07C 2523/06* (2013.01); *C07C 2523/26* (2013.01); *C07C 2523/72* (2013.01); *C07C 2523/80* (2013.01); *C07C 2529/85* (2013.01)

(58) Field of Classification Search
CPC ............ C07C 2523/06; C07C 2523/26; C07C 2523/42; C07C 2523/44; C07C 2523/46; C07C 2523/72; C07C 2523/80; C07C 2529/85; C07C 9/06; C07C 9/08; C07C 9/10; C07C 11/08; C07C 11/10
See application file for complete search history.

(56) References Cited

U.S. PATENT DOCUMENTS

| 4,472,535 A | 9/1984 | Chang et al. |
| 6,376,562 B1 | 4/2002 | Ihm et al. |
| 8,513,315 B2 | 8/2013 | Kibby |
| 2004/0151265 A1 | 8/2004 | Fisher et al. |
| 2007/0244000 A1 | 10/2007 | Molinier et al. |
| 2008/0319245 A1 | 12/2008 | Fujimoto et al. |

FOREIGN PATENT DOCUMENTS

| CN | 103071528 A | 5/2013 |
| CN | 103508828 A | 1/2014 |
| CN | 103772087 A | 5/2014 |
| EP | 2055380 A1 | 5/2009 |

(Continued)

OTHER PUBLICATIONS

Chen et al., "C2—C4 hydrocarbons synthesis from syngas over CuO—ZnO—Al2O3/SAPO-34 bifunctional catalyst," J. Chem. Technol. Biotechnol. 90(3)2015 415-422.
Chen et al., "Synthesis of CuO—ZnO—Al2O3 with SAPO-34 core and shell structured catalyst by intermediate layer method," Pure Appl. Chem. 2014, 86(5), 775-783.
Dawood et al., "Bifunctional catalysis: hydrocondensation of carbon monoxide on copper/zinc mordenite", Nouveau Journal de Chimie, 8 (1984) pp. 601-604.
Erena et al., "Study of physical mixtures of Cr2O3—ZnO and ZSM-5 catalysts for the transformation of syngas into liquid hydrocarbons," Ind. Eng. Chem. Res. 37 (1998) pp. 1211-1219.

(Continued)

*Primary Examiner* — Jafar Parsa
(74) *Attorney, Agent, or Firm* — Dinsmore & Shohl, LLP

(57) ABSTRACT

A feedstream comprising hydrogen and a gas selected from carbon monoxide, carbon dioxide, or a combination thereof is converted to a product mixture containing a combination of saturated and unsaturated two carbon atom and three carbon atom hydrocarbons via contact with a mixed catalyst comprising a mixed metal oxide catalyst selected from a copper oxide, copper oxide/zinc oxide, copper oxide/alumina, copper oxide/zinc oxide/alumina catalyst, a zinc oxide/chromium oxide catalyst, or a combination thereof, in admixture with a molecular sieve catalyst having a CHA, AEI, AEL, AFI, BEA, or DDR framework type, or a combination of such molecular sieves. Exemplary molecular sieve catalysts include SAPO-34, SAPO-18, SAPO-5, and Beta. Advantages include reduced production of C1 hydrocarbons, C4 and higher hydrocarbons, or both; long catalyst lifetimes; desirable conversions; and desirable proportions of C2 and C3 paraffins.

10 Claims, No Drawings

(56) References Cited

FOREIGN PATENT DOCUMENTS

| JP | 2009195815 A | 9/2009 |
|----|--------------|--------|
| WO | 2010068364 A2 | 6/2010 |

OTHER PUBLICATIONS

Fujimoto et al., "Selective synthesis of C2—C5 hydrocarbons from carbon dioxide utilizing a hybrid catalyst composed of a MeOH synthesis catalyst and zeolite," Applied Catalysis 31 (1987) 13-23M.

Fujimoto et al., "Synthesis gas conversion utilizing mixed catalyst composed of CO reducing catalyst and solid acid, IV. Selective synthesis of C2, C3, C4 paraffins from synthesis gas," Journal of Catalysis 94 (1985), 16-23.

Fujiwara et al. "Change of catalytic properties of FeZnO/zeolite composite catalyst in the hydrogenation of carbon dioxide," Applied Catalysis A: General 154 (1-2) (1997), 87-101.

Fujiwara et al., "Hydrocarbon synthesis from carbon dioxide and hydrogen over Cu—Zn—Cr oxide/zeolite hybrid catalysts," Journal of the Chemical Society, Chemical Communications 10 (1992) 767-768.

Fujiwara et al. "Hydrogenation of carbon dioxide over Fe—ZnO/zeolite composite catalysts," Chemistry Letters 1995, 24 (9), 839-840.

Fujiwara et al. "Development of composite catalysts made of Cu—Zn—Cr oxide/zeolite for the hydrogenation of carbon dioxide," Applied Catalysis A: General, 121 (1) (1995) 113-124.

Fujiwara et al. "Hydrogenation of carbon dioxide over Cu—Zn-chromate/zeolite composite catalyst: The effects of reaction behavior of alkenes on hydrocarbon synthesis," Applied Catalysis A: General 130 (1995) 105-116.

Inui et al. "Hydrogenation of carbon dioxide to C1—C7 hydrocarbons via MeOH on composite catalysts," Applied Catalysis A: General 94 (1993) (1) 31-44.

Jeon et al. "Selective synthesis of C3—C4 hydrocarbons through carbon dioxide hydrogenation on hybrid catalysts composed of a MeOH synthesis catalyst and SAPO," Applied Catalysis A: General 124 (1995) 91-106.

Li et al. "Direct synthesis of LPG from carbon dioxide over hybrid catalysts comprising modified MeOH synthesis catalyst and β-type zeolite," Applied Catalysis A: General 475 (2014) 155-160.

Lok et al., "Silicoaluminophosphate Molecular Sieves: Another New Class of Microporous Crystalline Inorganic Solids," J. Am. Chem. Soc. 106 (1984) 6092-6093.

Lunev et al. "Synthesis of iso-hydrocarbons mixture from CO2 and H2 on hybrid catalysts," Applied Organometallic Chemistry 15 (2001) 99-104.

Park et al., "Hydrocarbon synthesis through CO2 hydrogenation over CuZnOZrO2/zeolite hybrid catalysts," Catalysis Today 4 (1998) 165-173.

Simard et al., "ZnO—Cr2O3 + ZSM-5 catalylst with very low Zn/Cr ratio for the transformation of synthesis gas to hydrocarbons," Applied Catalysis A: General, 125 (1995) pp. 81-98.

Xiangang et al., "Direct synthesis of LPG from syngas derived from air-POM," Fuel 90 (2011), 2051-2054.

Yoo bet al., "Influence of solid acid catalyst on DME production directly from synthesis gas over the admixed catalyst of Cu/ZnO/Al/c L203 and various SAPO catalysts," Applied Catalysis A: General 330 (2007) 57-62.

Yu et al., "Transformation of syngas to light hydrocarbons over bifunctional CuO—ZnO/SAPO-34 catalysts: the effect of preparation methods," Reaction Kinetics Mechanisms and Catalysis, Apr. 26, 2014, 112, 489-497.

Zhang et al., "A highly stable and efficient catalyst for direct synthesis of LPG from syngas," Catalysis Letters (Jul. 2005), vol. 102, Nos. 12, 51-55.

Zhang et al., "Synthesis of LPG from synthesis gas," Fuel Processing Technology 85 (2004) 1139-1150.

CONVERSION OF CARBON MONOXIDE, CARBON DIOXIDE, OR A COMBINATION THEREOF OVER HYBRID CATALYST

The present application claims the benefit of U.S. Patent Application Ser. No. 62/023,500, filed on Jul. 11, 2014, entitled "CONVERSION OF SYNTHESIS GAS OVER HYBRID CATALYST," which is incorporated herein by reference in its entirety.

This invention relates generally to a process for converting a feedstream that comprises hydrogen and at least one gas selected from (1) carbon monoxide, (2) carbon dioxide, or (3) a combination thereof, into a product mixture that comprises a combination of saturated and unsaturated two and three carbon atom hydrocarbons, using a mixed catalyst.

For a number of industrial applications a desirable starting material is a lower hydrocarbon, including in particular $C_2$ and $C_3$ olefins, and/or $C_2$ and $C_3$ paraffins that can then be converted to olefins, for use in or as starting materials to produce plastics, fuels, and various downstream chemicals. These $C_2$ and $C_3$ materials may be saturated or unsaturated and therefore may include ethane, ethylene, propane, and/or propylene. A variety of methods of producing these lower hydrocarbons has been developed, including petroleum cracking and various synthetic processes.

Some of these synthetic processes begin with use of a hybrid catalyst. Different types of catalysts have also been explored, as well as different kinds of feedstreams and proportions of feedstream components. It is noted that certain inconsistencies in reference to mixed metal oxide-type catalysts are encountered in the art and are attributable to potential variations as to exact oxidation state(s) at the point of catalytic application, but researchers agree that any metal, such as, for example, copper (Cu), zinc (Zn), chromium (Cr), or zirconium (Zr), does, in a mixed metal oxide catalyst, exist in a non-elemental oxidation state, wherein such may or may not actually form an oxide, even if it is denominated herein for convenience as simply the metal itself. Researchers also agree that designation of a specific oxide, e.g., CuO, does not necessarily preclude the presence of an additional or different oxide of the given metal.

For example, in Park, Y.-K.; Park, K.-C.; Ihm, S.-K., "Hydrocarbon synthesis through $CO_2$ hydrogenation over $CuZnOZrO_2$/zeolite hybrid catalysts," *Catalysis Today* 44 (1998) 165-173, a catalyst including $Cu/ZnO/ZrO_2$ and a zeolite selected from ZSM-5, SAPO-34, and SAPO-5 is employed to hydrogenate a carbon dioxide ($CO_2$) and hydrogen ($H_2$) mixture.

U.S. Pat. No. 6,376,562 B1 (Ihm, et al.) also describes use of a hybrid catalyst, including a methanol synthesis catalyst and a methanol conversion catalyst. Experiments show conversion of $CO_2$ to hydrocarbons using a combination of $Cu/ZnO/ZrO_2$, either with SAPO-34 or SAPO-5, or with Cu/SAPO-34 or Cu/SAPO-5.

Another example may be found in Fujiwara, M.; Ando, H.; Matsumoto, M.; Matsumura, Y.; Tanaka, M.; Souma, Y., "Hydrogenation of carbon dioxide over Fe—ZnO/zeolite composite catalysts," *Chemistry Letters* 1995, 24 (9), 839-840, wherein $CO_2$ is hydrogenated over a combination of Fe—ZnO and HY zeolite. The reaction involves a methanol to gasoline reaction.

U.S. Patent Application Publication 2008/0319245 A1 (Fujimoto, et al.) describes a process for producing liquefied petroleum gas (hydrocarbon containing propane or butane as a main component) from carbon monoxide (CO) and $H_2$ with a catalyst which comprises a methanol synthesis component and a zeolite component. A preferable methanol synthesis component is an olefin-hydrogenation catalyst comprising a metal such as palladium (Pd) supported on a Zn—Cr based catalyst. The zeolite component may be a (Pd-supported) β-zeolite catalyst.

WO 2010/068364 A2 (Kibby, et al.) describes a process for converting syngas with a catalyst system comprising GaZSM-5 and ZnO—$Cr_2O_3$ to generate high octane hydrocarbons boiling in the gasoline range.

U.S. Pat. No. 8,513,315 B2 (Kibby, et al.), discloses $CO_2$ injection into synthesis feed gas to reduce or eliminate net $CO_2$ production during isosynthesis over a hybrid catalyst combining ZnO—$Cr_2O_3$ and ZSM-5. This produces high boiling hydrocarbons in the gasoline range.

Fujiwara, M.; Kieffer, R.; Ando, H.; Souma, Y., "Development of composite catalysts made of Cu—Zn—Cr oxide/zeolite for the hydrogenation of carbon dioxide," *Applied Catalysis A: General*, 121 (1) (1995) 113-124, discloses hydrogenation of $CO_2$ over a hybrid catalyst comprising Cu—Zn—Cr oxides and a dealuminated Y-type or H-ZSM-5 zeolite. The results suggest that hydrocarbon synthesis and the decomposition of methanol are competitive.

Fujiwara, M.; Ando, H.; Tanaka, M.; Souma, Y., "Hydrogenation of carbon dioxide over Cu—Zn-chromate/zeolite composite catalyst: The effects of reaction behavior of alkenes on hydrocarbon synthesis," *Applied Catalysis A: General* 130 (1995) 105-116, reports preparation of alkenes over a hybrid catalyst comprising uncalcined co-precipitated salts of copper, zinc and chromium and HY zeolite.

Fujimoto, K.; Shikada, T., "Selective synthesis of $C_2$-$C_5$ hydrocarbons from carbon dioxide utilizing a hybrid catalyst composed of a MeOH synthesis catalyst and zeolite," *Applied Catalysis* 31 (1987) 13-23, reports preparation of hydrocarbons from a mixture of $CO_2$, CO and $H_2$ over a hybrid catalyst comprising oxides of copper and zinc, or oxides of zinc and chromium, and a dealuminated Y type zeolite.

Fujiwara, M.; Kieffer, R.; Ando, H.; Xu, Q.; Souma, Y., "Change of catalytic properties of FeZnO/zeolite composite catalyst in the hydrogenation of carbon dioxide," *Applied Catalysis A: General* 154 (1-2) (1997), 87-101, reports hydrogenation of $CO_2$ over a mixture of oxides of iron and zinc, and a HY zeolite.

Fujiwara, M.; Souma, Y., "Hydrocarbon synthesis from carbon dioxide and hydrogen over Cu—Zn—Cr oxide/zeolite hybrid catalysts," *Journal of the Chemical Society, Chemical Communications* 10 (1992) 767-768, reports a combination of oxides of copper, zinc and chromium and zeolites for hydrocarbon synthesis.

Inui, T.; Kitagawa, K.; Takeguchi, T.; Hagiwara, T.; Makino, Y., "Hydrogenation of carbon dioxide to $C_1$-$C_7$ hydrocarbons via MeOH on composite catalysts," *Applied Catalysis A: General* 94 (1993) 14, 51-55, discloses use of a hybrid catalyst comprising CuCrZn or CuCrZnPdNa and ZSM-5. Reported results show a broad product distribution, ranging from $C_1$-$C_7$, and a high methane ($CH_4$) selectivity.

Inui, T.; Kitagawa, K.; Takeguchi, T.; Hagiwara, T.; Makino, Y., "Hydrogenation of carbon dioxide to $C_1$-$C_7$ hydrocarbons via MeOH on composite catalysts," *Applied Catalysis A: General* 94 (1993) (1) 31-44, reports hydrocarbon synthesis from $CO_2$ and $H_2$ via methanol over a hybrid catalyst comprising H-ZSM-5 and a Pd—Na-modified Cu—Cr—Zn oxide.

Jeon, J.-K.; Jeong, K.-E.; Park, Y.-K.; Ihm, S.-K., "Selective synthesis of $C_3$-$C_4$ hydrocarbons through carbon dioxide hydrogenation on hybrid catalysts composed of a MeOH synthesis catalyst and SAPO," *Applied Catalysis A: General* 124 (1995) 91-106, reports use of a hybrid catalyst comprising Cu/ZnO/ZrO$_2$ or Cu/ZnO/Al$_2$O$_3$ and a zeolite selected from ZSM-5, SAPO-5, and SAPO-44.

Li, C.; Yuan, X.; Fujimoto, K., "Direct synthesis of LPG from carbon dioxide over hybrid catalysts comprising modified MeOH synthesis catalyst and β-type zeolite," *Applied Catalysis A: General* 475 (2014) 155-160, reports production of C$_3$ and C$_4$ paraffins over a Zr-modified CuZn catalyst in combination with a Pd-modified Beta zeolite.

Lunev, N. K.; Shmyrko, Y. I.; Pavlenko, N. V.; Norton, B., "Synthesis of iso-hydrocarbons mixture from CO$_2$ and H$_2$ on hybrid catalysts," *Applied Organometallic Chemistry* 15 (2001) 99-104, reports formation of hydrocarbons ranging from C$_2$ to C$_{15}$ and beyond over a hybrid catalyst comprising a mixed metal oxide promoted with K and a Fe doped ZSM-11 zeolite.

Chinese Patent Publication (CN) 103508828A (Qing-jie Ge, et al.) discloses preparation of ethane and propane from syngas via a single-step conversion in the presence of a multi-functional catalyst. The multi-functional catalyst is a mixture of a CO hydrogenation catalyst and a molecular sieve catalyst modified with, e.g., palladium, platinum, ruthenium, rhodium, copper, iron, cobalt and/or manganese. The CO hydrogenation catalyst may be copper(II) oxide/zinc oxide/aluminum oxide (CuO/ZnO/Al$_2$O$_3$), copper/zirconium dioxide (Cu/ZrO$_2$), zinc oxide/-chromium(III) oxide (ZnO/Cr$_2$O$_3$), palladium/zinc oxide/chromium(III) oxide (Pd/ZnO/Cr$_2$O$_3$), and/or palladium/cerium(IV) oxide (Pd/CeO$_2$). Pressure is from 1-5 megapascals (MPa).

U.S. Pat. No. 4,472,535 (Chang, et al.) teaches conversion of synthesis gas to an exclusively hydrocarbon product with selectivity to ethane via use of a catalyst that comprises a zeolite (e.g., ZSM-5 and ZSM-11) and a metal component (e.g., palladium, thorium, platinum, iridium, copper, manganese, cobalt, chromium, zinc, rhodium or aluminum) distributed within the pore structure of the zeolite.

Japanese Patent Publication (JP) 2009195815 (Xiahong, et al.) discloses a catalyst for liquefied petroleum gas manufacture, wherein propane or butane is the main product. The catalyst comprises a copper-zinc-based methanol synthesis catalyst and a metal-modified zeolite that contains palladium, copper, chromium, manganese and/or iron.

U.S. Patent Application Publication 2007/0244000 (Molinier, et al.) discloses a process for producing an olefin product that involves converting syngas to an intermediate composition that is predominantly methanol (MeOH) and dimethyl ether (DME) using a catalyst including at least one metal oxide and at least one molecular sieve. The intermediate composition is then contacted with an olefin forming catalyst to form the olefin product. The metal oxide may include copper, silver, zinc, boron, magnesium, aluminum, vanadium, chromium, manganese, gallium, palladium, osmium or zirconium. The molecular sieve may be, for example, MCM-22, MCM-36, MCM-49, MCM-68, SAPO-11, SAPO-31 or SAPO-41.

Yoo, K. S., et al., "Influence of solid acid catalyst on DME production directly from synthesis gas over the admixed catalyst of Cu/ZnO/Al$_2$O$_3$ and various SAPO catalysts," *Applied Catalysis A: General* 330 (2007) 57, 57-62, discusses use of commercial Cu/Zn/Al$_2$O$_3$ (KATALCO™ 33-5) and SAPO catalysts (e.g., SAPO-5, SAPO-11 and SAPO-34). Direct DME synthesis conditions include a GHSV of 6000 milliliters per gram of catalyst*hour (mL/g-cat*h), 260° C. and 4.2 megapascals (MPa). These conditions are not shown to result in significant hydrocarbons production.

Fujimoto, K., et al., "Synthesis gas conversion utilizing mixed catalyst composed of CO reducing catalyst and solid acid, IV. Selective synthesis of C2, C3 and C4 paraffins from synthesis gas," *Journal of Catalysis* 94 (1985), 16-23, discloses use of hybrid catalysts composed of a physically mixed methanol synthesis catalyst (Pd/SiO$_2$) and Y-type zeolites with favorable conditions including a temperature of 300° C. to 350° C. and a pressure from 1.0 megapascals (MPa) to 5.1 MPa.

Zhang, Q., et al., "A highly stable and efficient catalyst for direct synthesis of LPG from syngas," *Catalysis Letters* (July 2005), Vol. 102, Nos. 12, 51-55, discloses direct synthesis of liquefied petroleum gas (LPG) from syngas over a hybrid catalyst that contains a methanol synthesis catalyst (PdCa/SiO$_2$) and a zeolite (β-zeolite).

Xiangang, M., et al., "Direct synthesis of LPG from syngas derived from air-POM," *Fuel* 90 (2011), 2051-2054, address use of syngas derived from partial oxidation of CH$_4$ with air (air-POM) using a hybrid catalyst consisting of a methanol synthesis catalyst and Y-zeolite that has been modified with palladium.

Zhang, Q., et al., "Synthesis of LPG from synthesis gas," *Fuel Processing Technology* 85 (2004) 1139-1150, relates to use of a hybrid catalyst consisting of a methanol synthesis catalyst and a zeolite in a fixed bed reactor to produce LPG from syngas. Methanol formed from syngas over a methanol synthesis catalyst is first converted into DME and then into hydrocarbons over a zeolite. The hybrid catalyst discussed in this reference consists of USY zeolite and a copper/zinc oxide methanol synthesis catalyst.

European Patent Application (EP) 2 055 380 A1 (Costa, et al.) relates to a process for producing hybrid catalysts for Fischer-Tropsch synthesis. The hybrid catalyst contains between 5 percent by weight (wt %) and 40 wt % cobalt, mixed with a bifunctional catalyst containing at least one Group VIB and/or Group VIII metal. The catalyst is carried on a support selected from zeolites, mesoporous silicoaluminates selected from MOR, FAU, BEA, ITQ-2 and ITQ-6 framework types, and mixed acid oxides of the type WO$_x$—ZrO$_2$.

Chen, Y., et al., "C$_2$-C$_4$ hydrocarbons synthesis from syngas over CuO—ZnO—Al$_2$O$_3$/SAPO-34 bifunctional catalyst," *J. Chem. Technol. Biotechnol.*, Jan. 9, 2014 (wileyonlinelibrary.com/jctb) DOI 10.1002/jctb.4309 (8 pages), discloses production of hydrocarbons from synthesis gas over a bifunctional catalyst containing methanol synthesis catalyst CuO/ZnO/Al$_2$O$_3$ and SAPO-34 zeolite. Production of C$_2$-C$_4$ hydrocarbons is balanced against coking via temperature alteration. Coking is shown after only 4 hours.

Chen, Y., et al., "Synthesis of CuO—ZnO—Al$_2$O$_3$ with SAPO-34 core and shell structured catalyst by intermediate layer method," *Pure Appl. Chem.* 2014, 86(5), 775-783 discloses preparation of a layered structure to increase selectivity in CO hydrogenation to produce light hydrocarbons.

Yu, Y., et al., "Transformation of syngas to light hydrocarbons over bifunctional CuO—ZnO/SAPO-34 catalysts: the effect of preparation methods," *Reaction Kinetics Mechanisms and Catalysis*, Apr. 26, 2014, 112, 489-497, discloses a bifunctional catalyst including CuO/ZnO and SAPO-34 prepared by two different methods. Different methods are found to have significant effect on catalyst performance, but the product obtained is not high in C2 and C3 paraffins.

Despite the obviously extensive research in this area, problems generally encountered include an unacceptable level of methanol remaining in the final product, an unacceptable level of methane, an unacceptable level of C$_4$ and higher products, or a combination thereof, requiring expensive separations in order to effectively utilize the C$_2$ and C$_3$ products for their intended purposes. Thus, there remains a need in the art for processes that are effective to produce $C_2$ and $C_3$ products, which also result in reduced amounts of methanol and/or $C_4$ and higher products, but which still enable desired levels of feedstream conversion. It is also desirable that a variety of feedstreams may be used resulting in essentially the same product distribution which reduces requirements for feedstream purity and/or feedstream costs. It is also desirable that any catalyst(s) used has/have desirably long lifetimes under processing conditions. Finally, it is desirable that such process minimizes or preferably does not involve production of an intermediate product stream of methanol, DME or other oxygenates which would then be separately converted to the desired hydrocarbon product, i.e., a $C_2$ and/or $C_3$ product.

In one embodiment the present invention provides a process for preparing $C_2$ and $C_3$ hydrocarbons comprising introducing a feedstream into a reactor, the feedstream comprising hydrogen ($H_2$) gas and a gas selected from carbon monoxide (CO), carbon dioxide ($CO_2$), and combinations thereof, such that the $H_2$ gas is present in an amount of from 10 volume percent (vol %) to 90 vol %, based on combined volumes of the $H_2$ gas and the gas selected from CO, $CO_2$, and combinations thereof; and contacting the feedstream and a mixed catalyst in the reactor, the mixed catalyst comprising as components a mixed metal oxide catalyst selected from a copper oxide catalyst, a copper oxide/zinc oxide catalyst, a copper oxide/alumina catalyst, a copper oxide/zinc oxide/alumina catalyst, a chromium oxide/zinc oxide catalyst, and combinations thereof; and a molecular sieve selected from molecular sieves having a framework type selected from CHA, AEI, AFI, AEL, BEA, and DDR framework types, and combinations thereof; the framework types corresponding to the naming convention of the International Zeolite Association; under reaction conditions sufficient to form a product mixture, the reaction conditions comprising a reactor temperature ranging from 300 degrees Celsius (° C.) to 440° C.; a pressure of at least 1 bar (100 kilopascals, kPa); and a gas hourly space velocity (GHSV) of at least 500 reciprocal hours ($h^{-1}$); the product mixture having, as calculated on a CO-free, $CO_2$-free, and $H_2$-free basis, a combined ethane and propane content that is more than 45 percent by weight (wt %); a methane content of less than 15 wt %; a combined butane and higher saturated hydrocarbon content of less than 30 wt %; and a combined unsaturated hydrocarbon and oxygenate content of less than 10 wt %; each weight percentage being based upon total product mixture weight and, when taken together, equaling 100 wt %.

The above process has utility in that it converts a feedstream that comprises, consists essentially of or consists of $H_2$ gas and a gas selected from CO, $CO_2$, or a combination thereof, to a product mixture that comprises a combination of saturated and unsaturated two carbon atom and three carbon atom hydrocarbons, such being primarily $C_2$ and $C_3$ paraffins. The product mixture itself has utility as a cracker feedstream to produce certain olefins and/or as a starting material or intermediate to produce a range of chemical products including plastics, fuels and the like.

It will be understood that CO or $CO_2$ may each be present in the feedstream as a sole second gas, or a combination of both may be present, in any proportion relative to one another. In other words, the feedstream may comprise, consist essentially of, or consist of, (1) a combination of CO and $H_2$, or (2) a combination of $CO_2$ and $H_2$, or (3) a combination of (1) and (2) (such being a combination of CO, $CO_2$, and $H_2$), and regardless of which embodiment is employed, such will react according to the process conditions of the invention to form a combination of saturated and unsaturated $C_2$ and $C_3$ products falling within the product mixture limitations. In all cases the outlet stream may contain CO, $CO_2$, and $H_2$ originating from either unconverted feed components or the Water Gas Shift reaction or its reverse.

Those skilled in the art will be able, with minimal experimentation, to ascertain the desired balance between feedstream composition and desired $C_2$ and $C_3$ products and proportions thereof within the product mixture limitations, as will be described further hereinbelow.

Where more than 50 mole-percent (mol %) of all carbon in the feedstream is initially in the form of CO, the CO may be said to be the primary carbon-containing constituent of the feedstream. In preferred embodiments such CO is present in an amount greater than 60 mol %, more preferably greater than 70 mol %, still more preferably greater than 80 mol %, and most preferably greater than 90 mol %. $H_2$ gas is separately measured and is desirably present in the feedstream in a volumetric ratio of $H_2$ to CO ($H_2$:CO) that is greater than or equal to 0.5:1, preferably greater than or equal to 0.6:1, more preferably greater than or equal to 1:1, still more preferably greater than or equal to 2:1, yet more preferably less than or equal to 10:1, still more preferably less than or equal to 7:1, and finally most preferably less than or equal to 3:1 to 6:1.

Where more than 50 mol % of all carbon in the feedstream is initially in the form of $CO_2$, the $CO_2$ may be said to be the primary carbon-containing constituent of the feedstream. In preferred embodiments such $CO_2$ is present in an amount greater than 60 mol %, more preferably greater than 70 mol %, still more preferably greater than 80 mol %, and most preferably greater than 90 mol %. $H_2$ gas is separately measured and is desirably present in the feedstream in a volumetric ratio of $H_2$ to $CO_2$ ($H_2$:$CO_2$) that is greater than or equal to 0.5:1, preferably greater than or equal to 0.6:1, more preferably greater than or equal to 1:1, still more preferably greater than or equal to 2:1, yet more preferably less than or equal to 10:1, still more preferably less than or equal to 9:1, and finally most preferably from 3:1 to 8:1.

In the process of the present invention, the selected feedstream is passed into a reactor via a heated reactor inlet, and in the reactor typically moves over and/or through a mixed catalyst bed under conditions sufficient to convert the carbon-containing gas (CO, $CO_2$, or a combination thereof) into the product mixture. The conditions under which this process may be carried out comprise, consist essentially of or consist of: (1) a reactor temperature ranging from 300° C. to 440° C.; (2) a pressure of at least 1 bar (0.1 megapascal (MPa)); and (3) a GHSV of at least 500 $h^{-1}$. As used herein, the phrase "reactor temperature" will be understood to represent either an average reactor temperature, where temperature is measured at more than one location within the reactor, or the sole temperature, where temperature is measured at only one location within the reactor. However, those skilled in the art will recognize that the temperature at different locations within the reactor will almost certainly vary somewhat, according to flow rates, catalyst flow and bed packing, reactor size and geometry, variation in reactor inlet temperatures, and so forth, and will be able to easily adjust process parameters and other means to control temperature, such as the use of a multi-tube heat exchanger, to ensure that the reactor temperature requirements of the present invention are met.

In certain particular embodiments, where the primary carbon-containing constituent of the feedstream, as defined hereinabove, is CO, such reaction conditions preferably comprise, consist essentially of or consist of: (1) a reactor temperature ranging from 350° C., more preferably from 360° C., and still more preferably from 370° C., to 440° C., more preferably to 410° C., and still more preferably to 390° C.; (2) a pressure of at least 20 bar (2.0 MPa), more preferably at least 35 bar (3.5 MPa), and still more preferably at least 50 bar (5.0 MPa); and (3) a GHSV from 500 $h^{-1}$, more preferably from 1000 $h^{-1}$, and still more preferably from 3000 $h^{-1}$, to 12000 $h^{-1}$, more preferably to 10000 $h^{-1}$, and still more preferably to 6000 $h^{-1}$.

In other embodiments, where the feedstream comprises carbon that is predominantly, as defined hereinabove, in the form of $CO_2$, such reaction conditions preferably comprise, consist essentially of or consist of: (1) a reactor temperature ranging from 300° C., more preferably from 320° C., and still more preferably from 330° C., to 400° C., more preferably to 390° C., and still more preferably to 380° C.; (2) a pressure of at least 2 bar (0.2 MPa), more preferably at least 28 bar (2.8 MPa), and still more preferably at least 40 bar (4.0 MPa); and (3) a GHSV from 500 $h^{-1}$, more preferably from 1000 $h^{-1}$, and still more preferably from 3000 $h^{-1}$, to 22000 $h^{-1}$, more preferably to 10000 $h^{-1}$, and still more preferably to 6000 $h^{-1}$.

The mixed catalyst bed comprises a mixed metal oxide catalyst, which is a mixed metal oxide so-called "methanol synthesis catalyst," comprising, consisting of, or consisting essentially of a mixed metal oxide selected from copper oxide, copper oxide/zinc oxide, copper oxide/alumina, copper oxide/zinc oxide/alumina or chromium oxide/zinc oxide, in admixture with a molecular sieve catalyst selected from molecular sieves having a framework type selected from CHA, AEI, AEL, AFI, BEA, and DDR framework types, and combinations of such molecular sieves. Examples of these may include, but are not necessarily limited to, CHA=SAPO-34, AlPO-34, and SSZ-13; AEI=SAPO-37, SAPO-11, SAPO-18, AlPO-18, AlPO-11 and SAPO-31; AFI=SAPO-5; AEL=SAPO-11 and AlPO-11; BEA=Beta; and DDR=ZSM-58. As the term is used herein, "SAPO" molecular sieves are defined as silicoaluminophosphate materials having a silicon content of at least 0.01 wt %, preferably at least 0.1 wt %, and more preferably at least 0.5 wt %. Many of these materials will have a silicon content of at least 5 wt % or greater. Thus, based upon this definition, molecular sieves that are primarily aluminophosphates, but actually contain very minor amounts of silicon, i.e., less than 0.01 wt %, would still be classified as "AlPO" molecular sieves. The molecular sieves listed hereinabove include a variety of eight- to twelve-membered ring molecules of varying pore size, configuration, and susceptibility to morphological alteration, but which are suitable, in combination with the listed mixed metal oxides and under the defined reaction conditions, of forming a product mixture falling within the given description limitations. Combinations of molecular sieves having any of the above framework types may also be employed.

In especially preferred embodiments the selected molecular sieve is non-metal-modified, i.e., it does not include in its crystal lattice any metal heteroatoms beyond those of which the lattice as a whole is composed. Thus, for example only, a silicoaluminate, e.g., a zeolite such as Beta, would not include any metal atom other than silicon and aluminum, and a silicoaluminophosphate, such as a SAPO, would not include any metal atom other than silicon, aluminum, and phosphorus.

With regard to specifically the SAPO silicoaluminophosphate molecular sieves, it will be understood by those skilled in the art that the elemental composition of the anhydrous form may be represented as $(Si_xAl_yP_z)O_2$, where x, y and z represent molar fractions of silicon, aluminum and phosphorus, with x+y+z=1. See, for example, Lok, B. M., et al., "Silicoaluminophosphate Molecular Sieves: Another New Class of Microporous Crystalline Inorganic Solids," *J. Am. Chem. Soc.* 106 (1984) 6092-6093. As noted above, use of a combination of these mixed metal oxides in admixture with a molecular sieve is also acceptable, and the mixed metal oxides may be made separately or together. The mixed metal oxide catalyst and the molecular sieve catalyst are preferably present in the reactor, typically as a mixed catalyst in a catalyst bed, in a weight/weight (wt/wt) ratio (mixed metal oxide catalyst:molecular sieve catalyst) ranging from 0.1:1 to 10:1, preferably from 0.5:1 to 9:1.

In one embodiment the mixed metal oxide catalyst is preferably a copper oxide catalyst wherein the copper content ranges from greater than 0 wt % to 90 wt %. In another embodiment the mixed metal oxide catalyst is preferably a copper oxide/zinc oxide catalyst wherein the copper and zinc contents each independently range from greater than 0 wt % to 90 wt %. In still another embodiment the mixed metal oxide catalyst is preferably a copper oxide/alumina catalyst wherein the copper content ranges from greater than 0 wt % to 90 wt % and the aluminum content ranges from greater than 0 wt % to 55 wt %. In yet another embodiment the mixed metal oxide catalyst is preferably a copper oxide/zinc oxide/alumina catalyst wherein the copper and zinc contents each independently range from greater than 0 wt % to 90 wt %, and the aluminum content ranges from greater than 0 wt % to 55 wt %. In still another embodiment the mixed metal oxide catalyst is preferably a chromium oxide/zinc oxide catalyst wherein the chromium and zinc contents independently range from greater than 0 wt % to 80 wt %. Each of the weight percents in this paragraph are based upon the combined weight percents of all metals in the mixed metal oxide. The oxygen in each catalyst is therefore present in an amount determined by subtracting the sum of the wt % of each of the component metals from 100 wt %.

It is additionally noted that the aluminum oxide, i.e., alumina, may be in any phase or combination of phases. However, there may in some embodiments be a preference for use of a gamma-alumina, or predominantly (more than 50 wt %) of gamma-alumina, the weight percent being based on total alumina. Other phases of aluminas, such as alpha-alumina, omega-alumina, eta-alumina, etc., may be used alternatively or as a component, preferably a minor component, with another alumina phase, such as a gamma phase.

The product mixture resulting from the inventive process, following contact between the feedstream and the mixed catalyst under the specified reaction conditions, may desirably be high in saturated and unsaturated $C_2$ and/or $C_3$ products, such as ethane, and/or propane, and/or ethylene and/or propylene; relatively low in $C_1$ products, such as $CH_4$; and relatively low in oxygenated products. In particular embodiments it is also relatively low in $C_4$ and higher products. In general the process shows improved selectivity of paraffin $C_2$ and $C_3$ products, i.e., ethane and propane.

More particularly, the product mixture, regardless of the precise composition of feedstream within the given definition, may be characterized as having, as calculated on a CO-free, $CO_2$-free basis, and $H_2$-free basis, a combined ethane and propane content that is more than 45 wt %; a methane content of less than 15 wt %; a combined butane and higher saturated hydrocarbon content of less than 30 wt %; and a combined unsaturated hydrocarbon and oxygenate content of less than 10 wt %.

In preferred embodiments, and again, as calculated on a CO-free, $CO_2$-free, and $H_2$-free basis, the combined ethane and propane content is more than 60 wt %; the methane content is less than 10 wt %; the combined butane and higher saturated hydrocarbon content is less than 25 wt %; and the combined unsaturated hydrocarbon and oxygenate content is less than 5 wt.

In addition to the above hydrocarbon values, the outlet stream will obviously contain both the product mixture and some proportion of unconverted gas selected from $H_2$, CO, $CO_2$, and combinations thereof, depending upon feedstream composition. The amount of each will vary according to a variety of factors well known to those skilled in the art, including carbon conversion, yield, catalyst productivity, time on stream, and so forth. This unconverted gas stream may be separated from the product mixture and, if desired, recycled back into the process again as a portion of the feedstream. Alternatively it may be vented or otherwise disposed of with appropriate equipment, such as scrubbers.

EXAMPLE 1

Physically mix 100 microliters (4) of a copper-zinc-aluminum mixed metal oxide catalyst that has a copper (Cu) content of 39 wt %, a zinc (Zn) content of 25 wt %, and an aluminum (Al) content of 10 wt % (HiFUEL™ R120) and 100 microliters (4) of a silicoaluminophosphate catalyst (SAPO-34) by shaking them together in a bottle. Each of the two catalysts has a particle size before mixing ranging from 40 mesh (0.422 millimeter (mm)) to 80 mesh (0.178 mm).

Activate the physically mixed catalyst using a 90/10 vol %/vol % mix of $H_2$ and nitrogen ($N_2$) at a GHSV of 6000 $h^{-1}$, a temperature of 280° C. and a pressure of 10 bar (1.0 MPa) for a period of three hours (3 hr). Use onset of activation as a reference point for Time-on-Stream (TOS)=0 hour (hr).

Pass a combination of CO and $H_2$ ($H_2$:CO ratio of 1) over the activated catalyst at a GHSV of 6000 $h^{-1}$ while maintaining the pressure at 10 bar (1.0 MPa) and using a screening test protocol varied in $H_2$:CO ratio and temperature (T) with a dwell time for each stage of 6 hr as follows:

TABLE 1

Process conditions for $CuO/ZnO/Al_2O_3$ + SAPO-34 catalyst.

| Stage | $H_2$:CO ratio (vol/vol) | T (° C.) |
| --- | --- | --- |
| 1 | 8.5 | 280 |
| 2 | 1 | 280 |
| 3 | 8.5 | 340 |
| 4 | 1 | 340 |
| 5 | 8.5 | 400 |
| 6 | 1 | 400 |

Data in Table 2 hereinbelow are (a) only for Stages 4 and 6; (b) based on analysis of a sample of gaseous reactor effluent; and (c) determined using a calculation convention wherein selectivity for each product is referenced only to detected products.

TABLE 2

Results for $CuO/ZnO/Al_2O_3$ + SAPO-34 catalyst.

| T (° C.) | Calculated CONV (mol %) | Calculated C1 SEL (mol %) | | Calculated C2 SEL (mol %) | | Calculated C3 SEL (mol %) | | Calculated C4 SEL (mol %) | | Other* (mol %) |
| --- | --- | --- | --- | --- | --- | --- | --- | --- | --- | --- |
| | | CO2 | CH4 | $C_{2H4}$ | C2H6 | C3H6 | C3H8 | C4H8 | C4H10 | |
| 340 | 6.0 | 66 | <1 | 1.5 | 8.9 | 5.9 | 16.6 | 0 | 0 | <0.1 |
| 400 | 18.3 | 51 | 3.8 | 0 | 18.4 | 5.8 | 20.1 | 0 | 0 | 0.9 |

*Represents oxygenates and any hydrocarbon that are otherwise below quantification limit (BQL).

Skilled artisans recognize that conversion of a combination of CO and $H_2$ may yield a number of unspecified by-products including some that can be deposited on the catalyst bed (e.g., as carbon or as waxes) and, as such, cannot be detected by gas chromatography (GC). A calculation of conversion and selectivity that appears to be more accurate references data to an absolute decrease in amount of CO passing through the reactor (designated herein as "absolute carbon conversion" and "absolute carbon selectivity"). Table 3 hereinbelow presents re-calculated results for Stages 3 through 6 of the above screening protocol. The re-calculated results reflect peak assignment corrections based upon use of a reference cylinder of known gas composition (a certified mixture of simple paraffins (lower hydrocarbons ($C_1$-$C_6$), with no isomers such as isobutane), olefins (no isomers such as 2-butene), CO, $CO_2$ and $H_2$ balanced to 100 vol % by $N_2$. The re-calculation indicates that the olefins reported in Table 2 are not actually olefins, and thus their values in Table 3 are corrected to zero.

TABLE 3

Results for CuO/ZnO/Al$_2$O$_3$ + SAPO-34 catalyst, re-calculated.

| T (° C.) | H$_2$:CO ratio | C CONV (mol %) | C$_1$ SEL (mol %) | | C$_2$ SEL (mol %) | | C$_3$ SEL (mol %) | | C$_4$ SEL (mol %) | | Other (mol %) |
|---|---|---|---|---|---|---|---|---|---|---|---|
| | | | CO$_2$ | CH$_4$ | C$_2$H$_4$ | C$_2$H$_6$ | C$_3$H$_6$ | C$_3$H$_8$ | C$_4$H$_8$ | C$_4$H$_{10}$ | |
| 340 | 8.5 | 28.2 | 41.4 | 5.7 | 0 | 10.1 | 0 | 21.1 | 0 | 6.4 | 13.3 |
| 340 | 1 | 6.3 | 30.9 | 0.3 | 0 | 4.1 | 0 | 8.5 | 0 | 2.9 | 46.7 |
| 400 | 8.5 | 46.3 | 37.5 | 7.2 | 0 | 24.2 | 0 | 26.4 | 0 | 4.7 | 0 |
| 400 | 1 | 18.2 | 41.8 | 3.1 | 0 | 14.8 | 0 | 17.8 | 0 | 4.9 | 17.6 |

The data in Table 3 demonstrate that the higher temperature shown (400° C.) improves the yield of C$_2$-C$_3$ hydrocarbons, by increasing both CO conversion and C$_2$-C$_3$ selectivity. The data also demonstrate that, for the conditions shown in this Example 1, an increase in H$_2$:CO ratio, while maintaining the same temperature, pressure and GHSV, leads to an increase in CO conversion, but with a higher selectivity to CH$_4$.

EXAMPLE 2

Replicate Example 1, but use four stages rather than six stages, with a H$_2$:CO ratio of 1, a process pressure of 10 bar (1.0 MPa), a GHSV of 6000 h$^{-1}$ and a dwell time of 6 hr per stage. Results are recorded in Table 4 hereinbelow.

TABLE 4

Results for CuO/ZnO/Al$_2$O$_3$ + SAPO-34 catalyst.

| Stage | T (° C.) | C CONV. (mol %) | C$_1$ SEL (mol %) | | C$_2$ SEL (mol %) | | C$_3$ SEL (mol %) | | C$_4$ SEL (mol %) | | Other (mol %) |
|---|---|---|---|---|---|---|---|---|---|---|---|
| | | | CO$_2$ | CH$_4$ | C$_2$H$_4$ | C$_2$H$_6$ | C$_3$H$_6$ | C$_3$H$_8$ | C$_4$H$_8$ | C$_4$H$_{10}$ | |
| 1 | 280* | 10.7 | 35.4 | 0 | 0 | 0.8 | 0 | 1.4 | 0 | **BQL | 62.4 |
| 2 | 340 | 5.3 | 45.1 | 3.7 | 0 | 7.3 | 0 | 10.1 | 0 | 1.1 | 32.7 |
| 3 | 360 | 7.3 | 50.5 | 3.5 | 0 | 19.4 | 0 | 23.8 | 0 | 2.8 | 0 |
| 4 | 380 | 13.8 | 48.1 | 1.6 | 0 | 22.0 | 0 | 25.0 | 0 | 3.3 | 0 |

*Outside of claimed temperature range.

**"Below Quantification Limit," an indication that with the GC apparatus used for this Example, a peak value is too small to be quantified.

The data in Table 4 demonstrate that a temperature in excess of 360° C. operates more effectively than a temperature of 360° C. or below to reduce CH$_4$ (C1 hydrocarbon) formation while improving carbon conversion and selectivity to C2 and C3 products, under the previously defined conditions of this Example 2. A comparison of this data with the data in Table 3 also shows that the overall selectivity to C2 and C3 products is higher at 380° C., 10 bar pressure, and a H$_2$:CO ratio of 1 than at 400° C., 10 bar (1.0 MPa) pressure, and a H$_2$:CO ratio of 1.

EXAMPLE 3

Replicate Example 2, but introduce a combination of CO and H$_2$ to the reactor only after the reactor temperature reaches a temperature of 380° C. Results are reported in Table 5 hereinbelow.

TABLE 5

Results for CuO/ZnO/Al2O3 + SAPO-34 catalyst at 380° C.

| C CONV. (mol %) | C$_1$ SEL (mol %) | | C$_2$ SEL (mol %) | | C$_3$ SEL (mol %) | | C$_4$ SEL (mol %) | | Other (mol %) |
|---|---|---|---|---|---|---|---|---|---|
| | CO$_2$ | CH$_4$ | C$_2$H$_4$ | C$_2$H$_6$ | C$_3$H$_6$ | C$_3$H$_8$ | C$_4$H$_8$ | C$_4$H$_{10}$ | |
| 24.3 | 46.8 | 0.9 | 0 | 17.9 | 0 | 27.3 | 0 | 6.8 | 0.3 |

A comparison of data among Tables 2-5 showing catalytic performance results for the same mixed ("hybrid") catalyst tested at pressure=10 bar, GHSV=6000 h$^{-1}$ and H$_2$:CO ratio=1 highlights a surprising and important effect on selectivity (less CH$_4$ and more C$_2$-C$_3$ in the product stream) and on activity (higher CO conversion) where the hybrid is prevented from exposure to the reactive feedstream at lower process temperatures (below 360° C.).

EXAMPLE 4

Replicate Example 3, but with the same catalyst being exposed to a combination of CO and H$_2$ that has a H$_2$:CO ratio=3, pressure=20 bar (2.0 MPa), reactor temperature of 380° C., with a dwell time of 12 hr. Results are summarized in Table 6 hereinbelow.

TABLE 6

Results for CuO/ZnO/Al$_2$O$_3$ + SAPO-34 catalyst.

| C CONV (mol %) | C$_1$ SEL (mol %) | | C$_2$ SEL (mol %) | | C$_3$ SEL (mol %) | | C$_4$ SEL (mol %) | | Other (mol %) |
|---|---|---|---|---|---|---|---|---|---|
| | CO$_2$ | CH$_4$ | C$_2$H$_4$ | C$_2$H$_6$ | C$_3$H$_6$ | C$_3$H$_8$ | C$_4$H$_8$ | C$_4$H$_{10}$ | |
| 64 | 40.7 | 1.7 | 0 | 17.6 | 0 | 28.4 | 0 | 7.9 | 3.7 |

The data in Table 6, in comparison with that in Table 5, demonstrate that process conditions may be varied within the scope of teachings presented herein while still obtaining significant improvement in carbon conversion without appreciable differences in C$_1$-C$_4$ selectivities.

EXAMPLE 5

A comparison of use of a CuO/ZnO/Cr$_2$O$_3$+SAPO-34 catalyst versus a Cr$_2$O$_3$/ZnO+SAPO-34 catalyst is carried out to determine the effect of CuO, as follows:

Mixed metal oxide (MMO) catalyst 5(a): Prepare a mixed metal oxide catalyst from copper nitrate, zinc nitrate and chromium nitrate precursors. Target elemental composition is Cu (10 mol %), Zn (45 mol. %) and chromium (Cr) (45 mol %).

MMO catalyst 5(b): Precursors are zinc nitrate and chromium nitrate. Target elemental composition is 50 mol % each of Zn and Cr.

Start preparation of each catalyst by vigorously mixing solutions of the precursors added in a proportion that targets the desired elemental composition defined hereinabove. Effect co-precipitation at ambient conditions (nominally 25° C. and one (1) atmosphere (atm, 1.01 bar, 98.1 kilopascals (kPa)) pressure by transferring 20 milliliters (mL) volume of mixed precursors to a vial containing 20 mL of ammonium hydroxide (Aldrich, 28-30% NH$_3$ basis). This results in a rapid co-precipitation of mixed hydroxides. During a follow-up aging stage (16 hr), subject the co-precipitate to constant orbital shaking (500 revolutions per minute (rpm)) and heating (100° C.) to yield a gel-like residue of mixed hydroxides and oxides. Finally, transfer the residue to an oven and calcine it under temperature-programmed conditions (static air, ramp 2° C./min to 550° C., dwell 5 hr at 550° C.). Crush and sieve the calcined residue to a desired particle size (from 40 mesh (0.422 mm) to 80 mesh (0.178 mm)).

Analysis by X-ray fluorescence of catalyst 5(a) gives an elemental oxide composition as follows: CuO 8.9 wt %, ZnO 43.1 wt %, and Cr$_2$O$_3$ 48.0 wt %, each wt % being based upon combined weight of CuO, ZnO and Cr$_2$O$_3$. X-ray fluorescence (XRF) analysis of catalyst 5(b) gives an elemental oxide composition as follows: 51 wt % ZnO and 49 wt % Cr$_2$O$_3$ each wt % being based upon combined weight of ZnO and Cr$_2$O$_3$.

Physically mix each catalyst independently (5(a) or 5(b)) with SAPO-34 as in Example 1, then activate the physical mix as in Example 1, but change the temperature of the reaction to 400° C. and 450° C., for physical mixtures SAPO-34/5(a) and SAPO-34/5(b), respectively, hereinafter denominated as hybrid catalysts HC-5a and HC-5b, respectively. The onset of the activation stage is herein a reference point for Time-on-Stream (TOS)=0 hours.

Pass a combination of CO and H$_2$ over the activated catalyst as in Example 1 using a process pressure (P) of 10 bar (1.0 MPa) and a temperature, GHSV and H$_2$:CO ratio as shown in Table 7a (for HC-5a) and Table 7b (for HC-5b). Tables 8a, 8b, and 8c show CO conversion and selectivity values for the given reactions.

TABLE 7a

Conditions for HC-5a (CuO/ZnO/Cr$_2$O$_3$ + SAPO-34 catalyst).

| Stage | H$_2$:CO ratio | Process T (° C.) | GHSV (h$^{-1}$) | Dwell time (hr) |
|---|---|---|---|---|
| 1 | 8.5 | 400 | 6000 | 12 |
| 2 | 1 | 400 | 6000 | 12 |
| 3 | 0.1 | 400 | 6000 | 6 |
| 4 | 8.5 | 450* | 6000 | 6.22 |
| 5 | 8.5 | 450* | 3000 | 6 |
| 6 | 1 | 450* | 6000 | 6 |
| 7 | 1 | 450* | 3000 | 6 |

*Outside claimed temperature range.

TABLE 7b

Conditions for HC-5b (Cr$_2$O$_3$/ZnO catalyst + SAPO-34 catalyst)

| Stage | H$_2$:CO ratio | Process T (° C.) | GHSV (hr$^{-1}$) | Dwell time (hr) |
|---|---|---|---|---|
| 1 | 8.5 | 400 | 6000 | 6 |
| 2 | 1 | 400 | 6000 | 6 |
| 3 | 0.1 | 400 | 6000 | 6 |
| 4 | 0.1 | 450* | 6000 | 2.19 |

*Outside claimed temperature range.

TABLE 8a

Stage 2 (400° C. and $H_2$:CO ratio = 1) for HC-5a, calculated using same method as in Table 2.

| Tentative C CONV* (mol %) | Tentative $C_1$ SEL** (mol %) | | Tentative $C_2$ SEL (mol %) | | Tentative $C_3$ SEL (mol %) | | Tentative $C_4$ SEL (mol %) | | Other (mol %) |
|---|---|---|---|---|---|---|---|---|---|
| | $CO_2$ | $CH_4$ | $C_2H_4$ | $C_2H_6$ | $C_3H_6$ | $C_3H_8$ | $C_4H_8$ | $C_4H_{10}$ | |
| 6.3 | 62.6 | 9.2 | 0 | 8.7 | 9.0 | 10.5 | <1 | 0 | 0 |

*Conversion
**Selectivity

TABLE 8b

HC-5a, corrected calculation using same method as in Table 3.

| T (° C.) | $H_2$:CO ratio | C CONV. | $CO_2$ | $CH_4$ | $C_2H_4$ | $C_2H_6$ | $C_3H_6$ | $C_3H_8$ | $C_4H_8$ | $C_4H_{10}$ | Other (mol %) |
|---|---|---|---|---|---|---|---|---|---|---|---|
| 400 | 8.5 | 14.4 | 41 | 19.6 | 0 | 4 | 1.6 | 9.5 | 0 | 0 | 24.3 |
| 400 | 1 | 6.8 | 41 | 6.1 | 0.3 | 5.8 | 5.8 | 6.9 | 0 | 0.6 | 26.7 |
| 400 | 0.1 | 1.2 | 30.6 | 0 | 0 | 0 | 4.6 | 0 | 0 | 0 | 64.8 |
| 450* | 8.5 | 22 | 35.2 | 33.9 | 0 | 10.6 | 0 | 7.3 | 0 | 0 | 13.0 |
| 450* | 8.5 | 31.1 | 29.7 | 31.6 | 0 | 4.1 | 0 | 4 | 0 | 0 | 30.6 |
| 450* | 1 | 8.7 | 31.4 | 11.5 | 0 | 7.1 | 1.3 | 5.7 | 0 | 0.8 | 42.2 |
| 450* | 1 | 13.3 | 25.5 | 10.1 | 0 | 5.4 | 0 | 4.1 | 0 | 0.6 | 54.3 |

*Outside claimed temperature range

TABLE 8c

HC-5b, calculated using same method as in Table 4.

| T (° C.) | $H_2$:CO ratio | C CONV. | $CO_2$ | $CH_4$ | $C_2H_4$ | $C_2H_6$ | $C_3H_6$ | $C_3H_8$ | $C_4H_8$ | $C_4H_{10}$ | Other (mol %) |
|---|---|---|---|---|---|---|---|---|---|---|---|
| 400 | 8.5 | 11.6 | 39.4 | 26.6 | 0 | 0.1 | 0.4 | 4.6 | 0 | 0 | 28.9 |
| 400 | 1 | 5.8 | 30.6 | 6.7 | 0 | 5.3 | 1.5 | 7.3 | 0 | 0 | 48.6 |
| 400 | 0.1 | 1.1 | 16.4 | 0 | 0 | 0 | 0 | 1.3 | 0 | 0 | 82.3 |
| 450* | 0.1 | 1.4 | 15.4 | 0 | 0 | 0.1 | 0 | 1.2 | 0 | 0 | 83.3 |

*Outside claimed temperature range.

The data in Tables 8b and 8c demonstrate that the chromium-based mixed metal oxide catalyst ($Cr_2O_3$/ZnO, HC-5b) gives acceptable results when mixed with SAPO-34 at 400° C. (Table 8c), although its yield of C2 and C3 paraffins is lower than that of the CuO/ZnO/$Cr_2O_3$ catalyst (HC-5a) under similar conditions (Table 8b). Thus, the inclusion of the CuO in catalyst HC-5a offers a significant benefit.

COMPARATIVE EXAMPLES A and B

Replicate Example 1 with changes to temperature, pressure and GHSV as shown in Tables 9-A and 9-B hereinbelow. Change the amount of HiFUEL™ R120 and SAPO-34 to 500 μL for each catalyst and use a combination of CO and $H_2$ having a $H_2$:CO ratio=1. Tables 9-A and 9-B indicate catalyst performance results obtained during two distinct tests, during which conditions are varied as the test proceeds.

In the first test (Table 9-A for Comparative Example A), initiate exposure of the activated catalyst to a combination of CO and $H_2$ at a temperature of 280° C., pressure of 42 bar (4.2 megapascals (MPa)) and GHSV 7200 $h^{-1}$. As shown in Table 9-A, this combination of conditions yields a comparatively low conversion with no observed production of hydrocarbons (only $CO_2$ and oxygenates). In a second step, increase the temperature to 310° C. at the same conditions. In a third step, increase the temperature to 340° C. at the same conditions. In a fourth step, increase the temperature to 370° C. at the same conditions. In a fifth and final step, increase the temperature to 400° C. at the same conditions.

In the second test (Table 9-B for Comparative Example B), start exposure of the activated catalyst to the combination of CO and $H_2$ at a temperature of 340° C., and the same pressure and GHSV as in the first test. In a second step, decrease the GHSV to 3600 $h^{-1}$ at the same conditions. In a third step, decrease the pressure to 30 bar (3.0 MPa). In a fourth step, increase the temperature to 360° C. In a fifth step, decrease the pressure to 20 bar (2.0 MPa). In a sixth and final step, increase the temperature to 380° C.

TABLE 9-A

| T (° C.) | Run time (hr) | C CONV (mol %) | C$_1$ SEL (mol %) | | C$_2$ SEL (mol %) | | C$_3$ SEL (mol %) | | C$_4$ SEL (mol %) | | Other (mol %) |
|---|---|---|---|---|---|---|---|---|---|---|---|
| | | | CO$_2$ | CH$_4$ | C$_2$H$_4$ | C$_2$H$_6$ | C$_3$H$_6$ | C$_3$H$_8$ | C$_4$H$_8$ | C$_4$H$_{10}$ | |
| 280* | 16 | 9.3 | 20.3 | 0.0 | 0.0 | 0.0 | 0.0 | 0.0 | 0.0 | 0.0 | 79.7 |
| 310 | 26.2 | 15.3 | 29.6 | 0.6 | 0.0 | 1.0 | 0.0 | 0.6 | 0.0 | 0.0 | 68.2 |
| 340 | 29.8 | 16.9 | 33.7 | 1.9 | 0.0 | 1.7 | 0.0 | 1.3 | 0.0 | 0.0 | 61.0 |
| 370 | 34.7 | 14.1 | 36.0 | 4.5 | 0.0 | 3.0 | 0.0 | 3.3 | 0.0 | 0.0 | 53.2 |
| 400 | 39.8 | 11.1 | 43.5 | 7.3 | 0.3 | 12.4 | 0.0 | 14.7 | 0.0 | 0.0 | 25.8 |

*Outside claimed temperature range.

TABLE 9-B

| T (° C.) | P (bar/MPa) | Run time (hr) | C CONV (mol %) | C$_1$ SEL (mol %) | | C$_2$ SEL (mol %) | | C$_3$ SEL (mol %) | | C$_4$ SEL (mol %) | | Other (mol %) |
|---|---|---|---|---|---|---|---|---|---|---|---|---|
| | | | | CO$_2$ | CH$_4$ | C$_2$H$_4$ | C$_2$H$_6$ | C$_3$H$_6$ | C$_3$H$_8$ | C$_4$H$_8$ | C$_4$H$_{10}$ | |
| 340 | 42/4.2 | 12.6 | 22.2 | 34.7 | 1.5 | 0 | 2.6 | 0 | 3.9 | 0 | 1.6 | 55.7 |
| 340 | 42/4.2 | 30.9 | 22.2 | 36.8 | 1.8 | 0 | 1.3 | 0 | 1.3 | 0 | 0.7 | 58.1 |
| 340 | 30/3.0 | 42.4 | 13.9 | 33.1 | 1.8 | 0 | 1.2 | 0 | 1.6 | 0 | 0 | 62.3 |
| 360 | 30/3.0 | 59.3 | 10.7 | 36.5 | 3 | 0 | 4.6 | 0 | 6.5 | 0 | 0 | 49.4 |
| 360 | 20/2.0 | 76.2 | 6.6 | 43.2 | 2.5 | 0 | 12 | 0 | 14.7 | 0 | 2.1 | 25.5 |
| 380 | 20/2.0 | 87.2 | 11.6 | 48.2 | 1.8 | 0.7 | 19.3 | 3.3 | 21.8 | 0 | 4.7 | 0.2 |

The data in Tables 9-A and 9-B show that an initial less preferred reactor temperature has an impact on catalyst performance when the reactor is later brought to some of the more preferred temperature conditions.

EXAMPLE 6

Physically mix a copper-zinc-aluminum mixed metal oxide catalyst, having a copper (Cu) content of 39 wt %, a zinc (Zn) content of 25 wt %, and an aluminum content of 10 wt % (HiFUEL™ R120), and a silicoaluminophosphate catalyst (SAPO-34) by shaking them together in a bottle. Each of the catalysts has a particle size before mixing within a range of from 40 mesh (0.422 mm) to 80 mesh (0.178 mm). Activate the physically mixed catalyst using a pure hydrogen stream at a flow of 100 milliliters per minute (mL/min), a temperature of 270° C. and a pressure of 10 bar (1.0 MPa) for a period of 6 hr. Pressurize the system with pure N$_2$ up to the intended operating pressure. Heat up the system to the intended operating temperature while still flowing pure N$_2$ gas. Switch off the flow of N$_2$ and start passing the desired feed mix over the activated catalyst.

Tables 10-A1 through 10-F3 demonstrate how variations in a parameter, such as temperature in Tables 10-A1 and 10-A2, affect CO conversion and product selectivity.

TABLE 10-A1

Temperature screening at a pressure of 20 bar (2.0 MPa), a GHSV of 4000 h$^{-1}$, a H$_2$/CO ratio of 3 and a catalyst wt ratio of HiFUEL R120/SAPO-34 of 3

| T (° C.) | TOS (hr) | CO CONV (mol %) | C$_1$ Sel (mol %) | | C$_2$ Sel (mol %) | | C$_3$ Sel (mol %) | | C$_4$ Sel (mol %) | | Oxygenates Sel (mol %) | | Other (mol %) |
|---|---|---|---|---|---|---|---|---|---|---|---|---|---|
| | | | CO$_2$ | CH$_4$ | C$_2$H$_4$ | C$_2$H$_6$ | C$_3$H$_6$ | C$_3$H$_8$ | C$_4$H$_8$ | C$_4$H$_{10}$ | DME | MeOH | |
| 330* | 10 | 61 | 43.1 | 1.8 | 0 | 14.2 | 0.1 | 25 | 0 | 8.2 | 0.5 | 0.3 | 11.0 |
| 330* | 50 | 14.5 | 31.7 | 3.9 | 0 | 1.8 | 0 | 1.8 | 0 | 1.1 | 53.8 | 5.9 | 0 |
| 340* | 10 | 68.5 | 41.2 | 1.1 | 0 | 14.6 | 0 | 26.1 | 0 | 8.5 | 0 | 0.1 | 9.4 |
| 340* | 50 | 14.3 | 33.6 | 5.5 | 0 | 3.3 | 0 | 4.2 | 0 | 1.4 | 53.2 | 3.8 | 5.0 |
| 350* | 10 | 66.1 | 41.2 | 1.1 | 0 | 15.2 | 0 | 26.6 | 0 | 8.5 | 0 | 0.1 | 7.3 |
| 350* | 50 | 13.2 | 34.7 | 6.1 | 0 | 4.6 | 0 | 6.5 | 0 | 1.7 | 43.5 | 2.9 | 0 |
| 360 | 10 | 64.6 | 42.3 | 1 | 0 | 16.6 | 0 | 27.5 | 0 | 8.4 | 0 | 0.1 | 4.9 |
| 360 | 50 | 52.6 | 42.6 | 1.1 | 0 | 16.1 | 0 | 27.8 | 0 | 8.1 | 0.1 | 0.1 | 4.0 |
| 370 | 10 | 59.4 | 41 | 1.2 | 0 | 16.5 | 0 | 26.6 | 0 | 8.6 | 0 | 0.1 | 5.0 |
| 370 | 50 | 50.1 | 42.9 | 1.3 | 0 | 17 | 0 | 28.2 | 0 | 8.2 | 0 | 0.1 | 2.3 |
| 380 | 10 | 50.7 | 42.6 | 1.2 | 0 | 18.4 | 0 | 27.2 | 0 | 8 | 0 | 0.1 | 2.5 |
| 380 | 50 | 36.5 | 45.1 | 2 | 0 | 18.0 | 0.1 | 27.5 | 0 | 7.0 | 0.1 | 0.2 | 0 |
| 400 | 10 | 39.7 | 40 | 2.9 | 0 | 17.6 | 0 | 23.3 | 0 | 7.2 | 0 | 0 | 9.0 |
| 400 | 50 | 30.4 | 41.7 | 3.5 | 0 | 17.9 | 0.1 | 24.2 | 0 | 6.5 | 0 | 0 | 8.1 |
| 410 | 10 | 33.6 | 41.2 | 4.2 | 0 | 19.5 | 0 | 23.3 | 0 | 6.7 | 0 | 0 | 5.1 |
| 410 | 50 | 24 | 39.3 | 6.4 | 0.2 | 17.5 | 0.2 | 20.5 | 0 | 4.8 | 0 | 0 | 11.1 |
| 430 | 10 | 19.1 | 40 | 11 | 0 | 18.9 | 0 | 17.7 | 0 | 4.2 | 0 | 0.1 | 8.1 |
| 430 | 50 | 9.3 | 41.7 | 25.4 | 1.1 | 21.6 | 0.4 | 8.9 | 0 | 1.3 | 0.5 | 0.2 | 0.3 |

*Comparative data

TABLE 10-A2

($CO_2$ free selectivities and $CO_2$ inclusive selectivities)
Temperature screening at a pressure of 20 bar (2.0 MPa), a GHSV of 4000 h−1, a
$H_2$/CO ratio of 3 and a catalyst wt ratio of HiFUEL R120/SAPO-34 of 3

| | $CO_2$ free selectivities | | | | $CO_2$ inclusive selectivities | | | | |
|---|---|---|---|---|---|---|---|---|---|
| T (° C.) | (wt %) $CH_4$ | (wt %) $C_2H_6 + C_3H_8$ | (wt %) $C_4H_{10}$ | (wt %) Oxygenates + olefins | (wt %) $CO_2$ | (wt %) $CH_4$ | (wt %) $C_2H_6 + C_3H_8$ | (wt %) $C_4H_{10}$ | (wt %) Oxygenates + olefins |
| 330* | 4 | 77 | 16 | 3 | 72 | 1 | 22 | 4 | 1 |
| 330* | 4 | 4 | 1 | 91 | 46 | 2 | 2 | 1 | 49 |
| 340* | 2 | 81 | 17 | 0 | 71 | 1 | 24 | 5 | 0 |
| 340* | 6 | 7 | 1 | 86 | 49 | 3 | 4 | 1 | 44 |
| 350* | 2 | 81 | 16 | 0 | 70 | 1 | 24 | 5 | 0 |
| 350* | 7 | 12 | 2 | 79 | 52 | 4 | 6 | 1 | 38 |
| 360 | 2 | 82 | 15 | 0 | 70 | 1 | 25 | 5 | 0 |
| 360 | 2 | 82 | 15 | 1 | 70 | 1 | 24 | 4 | 0 |
| 370 | 2 | 81 | 16 | 0 | 70 | 1 | 25 | 5 | 0 |
| 370 | 3 | 82 | 15 | 0 | 70 | 1 | 25 | 4 | 0 |
| 380 | 2 | 83 | 14 | 0 | 70 | 1 | 25 | 4 | 0 |
| 380 | 4 | 82 | 12 | 1 | 71 | 1 | 24 | 4 | 0 |
| 400 | 6 | 80 | 14 | 0 | 70 | 2 | 24 | 4 | 0 |
| 400 | 7 | 80 | 12 | 0 | 70 | 2 | 24 | 4 | 0 |
| 410 | 8 | 79 | 12 | 0 | 69 | 3 | 24 | 4 | 0 |
| 410 | 14 | 76 | 9 | 1 | 70 | 4 | 23 | 3 | 0 |
| 430 | 22 | 69 | 8 | 0 | 69 | 7 | 21 | 2 | 0 |
| 430 | 44 | 49 | 2 | 4 | 67 | 15 | 17 | 1 | 1 |

*Comparative data

TABLE 10-B1

Pressure screening at a temperature of 380° C., a GHSV of 4000 hr$^{-1}$,
a $H_2$/CO ratio of 3, and a catalyst wt ratio of HiFUEL R120/SAPO-34 of 3

| P (bar/kPa) | TOS (hr) | CO CONV (mol %) | $CO_2$ (mol %) | $CH_4$ (mol %) | $C_2$ Sel (mol %) $C_2H_4$ | $C_2$ Sel (mol %) $C_2H_6$ | $C_3$ Sel (mol %) $C_3H_6$ | $C_3$ Sel (mol %) $C_3H_8$ | $C_4$ Sel (mol %) $C_4H_8$ | $C_4$ Sel (mol %) $C_4H_{10}$ | Oxygenates Sel (mol %) DME | Oxygenates Sel (mol %) MeOH | Other (mol %) |
|---|---|---|---|---|---|---|---|---|---|---|---|---|---|
| 5/500 | 10 | 3.1 | 28.9 | 8.5 | 0 | 9.2 | 0 | 7.8 | 0 | 0 | 0.3 | 0 | 45.3 |
| 5/500 | 50 | 2.3 | 27 | 16.2 | 0 | 7.9 | 0 | 3 | 0 | 0 | 0.4 | 0 | 45.4 |
| 20/2000 | 10 | 50.7 | 42.6 | 1.2 | 0 | 18.4 | 0 | 27.2 | 0 | 8 | 0 | 0.1 | 2.2 |
| 20/2000 | 50 | 36.5 | 44.6 | 2 | 0 | 18.2 | 0.1 | 26.7 | 0 | 7.1 | 0.1 | 0.2 | 0 |
| 35/3500 | 10 | 74 | 36.9 | 1.9 | 0 | 16.5 | 0 | 27.3 | 0 | 8.3 | 0 | 0.1 | 9.0 |
| 35/3500 | 50 | 70.1 | 38.9 | 1.8 | 0 | 16.5 | 0 | 28.7 | 0 | 8.3 | 0 | 0.1 | 5.7 |
| 50/5000 | 10 | 81.4 | 35.1 | 2.7 | 0 | 16 | 0 | 28.7 | 0 | 8.6 | 0 | 0.2 | 8.7 |
| 50/5000 | 50 | 79.4 | 36.5 | 2.6 | 0 | 15.6 | 0 | 29.7 | 0 | 8.8 | 0 | 0.2 | 6.6 |

TABLE 10-B2

($CO_2$ free selectivities and $CO_2$ inclusive selectivities) - Pressure screening at a temperature of
380° C., a GHSV of 4000 h$^{-1}$, a $H_2$/CO ratio of 3 and a catalyst wt ratio of HiFUEL R120/SAPO-34 of 3

| | $CO_2$ free selectivities | | | | $CO_2$ inclusive selectivities | | | | |
|---|---|---|---|---|---|---|---|---|---|
| P (bar/MPa) | (wt %) $CH_4$ | (wt %) $C_2H_6 + C_3H_8$ | (wt %) $C_4H_{10}$ | (wt %) Oxygenates + olefins | (wt %) $CO_2$ | (wt %) $CH_4$ | (wt %) $C_2H_6 + C_3H_8$ | (wt %) $C_4H_{10}$ | (wt %) Oxygenates + olefins |
| 5/0.5 | 34 | 64 | 0 | 2 | 76 | 8 | 15 | 0 | 0 |
| 5/0.5 | 60 | 38 | 0 | 2 | 73 | 16 | 10 | 0 | 1 |
| 20/2.0 | 2 | 83 | 14 | 0 | 70 | 1 | 25 | 4 | 0 |
| 20/2.0 | 4 | 82 | 12 | 1 | 71 | 1 | 24 | 4 | 0 |
| 35/3.5 | 4 | 81 | 15 | 0 | 67 | 1 | 27 | 5 | 0 |
| 35/3.5 | 4 | 81 | 15 | 0 | 68 | 1 | 26 | 5 | 0 |
| 50/5.0 | 5 | 79 | 15 | 1 | 65 | 2 | 28 | 5 | 0 |
| 50/5.0 | 5 | 79 | 15 | 1 | 66 | 2 | 27 | 5 | 0 |

TABLE 10-C1

H$_2$/CO volumetric feed ratio screening at a temperature of 380° C., a pressure of 50 bar (5.0 MPa), a GHSV of 4000 h$^{-1}$, a H$_2$/CO ratio of 3 and a catalyst wt ratio of HiFUEL R120/SAPO-34 of 3

| H$_2$/CO v-ratio | TOS (hr) | CO CONV (mol %) | C$_1$ Sel (mol %) CO$_2$ | C$_1$ Sel (mol %) CH$_4$ | C$_2$ Sel (mol %) C$_2$H$_4$ | C$_2$ Sel (mol %) C$_2$H$_6$ | C$_3$ Sel (mol %) C$_3$H$_6$ | C$_3$ Sel (mol %) C$_3$H$_8$ | C$_4$ Sel (mol %) C$_4$H$_8$ | C$_4$ Sel (mol %) C$_4$H$_{10}$ | Oxygenates Sel (mol %) DME | Oxygenates Sel (mol %) MeOH | Other (mol %) |
|---|---|---|---|---|---|---|---|---|---|---|---|---|---|
| 2 | 10 | 82.3 | 38.8 | 2.1 | 0 | 15.4 | 0 | 27.6 | 0 | 8 | 0 | 0.1 | 8.0 |
| 2 | 50 | 77.5 | 40.2 | 2.2 | 0 | 14.6 | 0 | 27.1 | 0 | 7.9 | 0 | 0.1 | 7.9 |
| 3 | 10 | 81.4 | 35.1 | 2.7 | 0 | 16 | 0 | 28.7 | 0 | 8.6 | 0 | 0.2 | 8.7 |
| 3 | 50 | 79.4 | 36.5 | 2.6 | 0 | 15.6 | 0 | 29.7 | 0 | 8.8 | 0 | 0.2 | 6.6 |
| 4 | 10 | 80 | 31.3 | 3.6 | 0 | 16.9 | 0 | 30.9 | 0 | 9 | 0 | 0.1 | 8.7 |
| 4 | 50 | 79.5 | 31.1 | 3.3 | 0 | 16.3 | 0 | 31.2 | 0 | 8.8 | 0 | 0.1 | 9.2 |
| 5 | 10 | 79.6 | 29.3 | 3.8 | 0 | 15.9 | 0 | 31.5 | 0 | 9.4 | 0 | 0.2 | 8.9 |
| 5 | 50 | 78 | 30.7 | 3.4 | 0 | 16.1 | 0 | 32.7 | 0 | 9.4 | 0 | 0.2 | 7.5 |
| 6 | 10 | 78.7 | 26.9 | 4.7 | 0 | 16.4 | 0 | 32.1 | 0 | 9.5 | 0 | 0.2 | 10.2 |
| 6 | 50 | 76.9 | 28.4 | 4.3 | 0 | 16.7 | 0 | 33.4 | 0 | 9.6 | 0 | 0.2 | 7.4 |

TABLE 10-C2

(CO$_2$ free selectivities and CO$_2$ inclusive selectivity) - H$_2$/CO feed ratio screening at a temperature of 380° C., a pressure of 50 bar (5.0 MPa), a GHSV of 4000 h$^{-1}$, and a catalyst wt ratio of HiFUEL R120/SAPO-34 of 3

| H$_2$:CO ratio | CO2 free selectivities (wt %) CH$_4$ | CO2 free selectivities (wt %) C$_2$H$_6$ + C$_3$H$_8$ | CO2 free selectivities (wt %) C$_4$H$_{10}$ | CO2 free selectivities (wt %) Oxygenates + olefins | CO2 inclusive selectivities (wt %) CO$_2$ | CO2 inclusive selectivities (wt %) CH$_4$ | CO2 inclusive selectivities (wt %) C$_2$H$_6$ + C$_3$H$_8$ | CO2 inclusive selectivities (wt %) C$_4$H$_{10}$ | CO2 inclusive selectivities (wt %) Oxygenates + olefins |
|---|---|---|---|---|---|---|---|---|---|
| 2 | 4 | 81 | 15 | 0 | 68 | 1 | 25 | 5 | 0 |
| 2 | 5 | 80 | 15 | 0 | 70 | 1 | 24 | 5 | 0 |
| 3 | 5 | 79 | 15 | 1 | 65 | 2 | 28 | 5 | 0 |
| 3 | 5 | 79 | 15 | 1 | 66 | 2 | 27 | 5 | 0 |
| 4 | 6 | 79 | 15 | 0 | 61 | 3 | 31 | 6 | 0 |
| 4 | 6 | 79 | 14 | 0 | 61 | 2 | 31 | 6 | 0 |
| 5 | 7 | 77 | 15 | 1 | 59 | 3 | 32 | 6 | 0 |
| 5 | 6 | 79 | 15 | 1 | 60 | 2 | 32 | 6 | 0 |
| 6 | 8 | 77 | 15 | 1 | 56 | 4 | 34 | 6 | 0 |
| 6 | 7 | 78 | 15 | 1 | 57 | 3 | 34 | 6 | 0 |

TABLE 10-D1

Cat weight (wt) ratio HiFUEL R120/SAPO-34 (screening at a temperature of 380° C., GHSV of 4000 h−1, and a H$_2$/CO ratio of 3

| P (bar/MPa) | Cat wt ratio | TOS (hr) | CO CONV (mol %) | C$_1$ Sel (mol %) CO$_2$ | C$_1$ Sel (mol %) CH$_4$ | C$_2$ Sel (mol %) C$_2$H$_4$ | C$_2$ Sel (mol %) C$_2$H$_6$ | C$_3$ Sel (mol %) C$_3$H$_6$ | C$_3$ Sel (mol %) C$_3$H$_8$ | C$_4$ Sel (mol %) C$_4$H$_8$ | C$_4$ Sel (mol %) C$_4$H$_{10}$ | Oxygenates Sel (mol %) DME | Oxygenates Sel (mol %) MeOH | Other (mol %) |
|---|---|---|---|---|---|---|---|---|---|---|---|---|---|---|
| 20/2.0 | 1 | 10 | 43.1 | 42.5 | 1.3 | 0 | 17.5 | 0.1 | 25.8 | 0 | 7.8 | 0 | 0.1 | 4.9 |
| 20/2.0 | 1 | 50 | 27.2 | 43 | 1.9 | 0 | 16.4 | 0.4 | 25.2 | 0 | 6.2 | 0 | 0.1 | 6.8 |
| 20/2.0 | 3 | 10 | 50.7 | 42.6 | 1.2 | 0 | 18.4 | 0 | 27.2 | 0 | 8 | 0 | 0.1 | 2.5 |
| 20/2.0 | 3 | 50 | 36.5 | 45.1 | 2 | 0 | 18.0 | 0.1 | 27.5 | 0 | 7.0 | 0.1 | 0.2 | 0 |
| 20/2.0 | 9.1 | 10 | 50.3 | 42.4 | 1.9 | 0 | 17.7 | 0 | 27 | 0 | 8.3 | 0 | 0.1 | 2.6 |
| 20/2.0 | 9.1 | 50 | 37 | 43.3 | 2.5 | 0 | 17 | 0 | 26.7 | 0 | 7.4 | 0 | 0.2 | 2.9 |
| 20/2.0 | 27.3 | 10 | 31.5 | 41 | 6.4 | 0 | 14.7 | 0 | 22.9 | 0 | 6.5 | 0.2 | 0.3 | 8.0 |
| 20/2.0 | 27.3 | 50 | 13.9 | 36.1 | 18.5 | 0 | 8.3 | 0 | 10.6 | 0 | 2.8 | 6.7 | 1.3 | 15.7 |
| 50/5.0 | 1.2 | 10 | 77.9 | 35.4 | 3 | 0 | 14.9 | 0 | 27.5 | 0 | 8.2 | 0 | 0.2 | 10.8 |
| 50/5.0 | 1.2 | 50 | 69.9 | 38.1 | 2.5 | 0 | 14.9 | 0 | 29 | 0 | 8.5 | 0.1 | 0.3 | 6.6 |
| 50/5.0 | 3 | 10 | 81.4 | 35.1 | 2.7 | 0 | 16 | 0 | 28.7 | 0 | 8.6 | 0 | 0.2 | 8.7 |
| 50/5.0 | 3 | 50 | 79.4 | 36.5 | 2.6 | 0 | 15.6 | 0 | 29.7 | 0 | 8.8 | 0 | 0.2 | 6.6 |
| 50/5.0 | 9.1 | 10 | 81.2 | 35.5 | 4 | 0 | 15.7 | 0 | 29.3 | 0 | 8.7 | 0.2 | 0.2 | 6.4 |
| 50/5.0 | 9.1 | 50 | 29.8 | 35.4 | 18.0 | 0 | 5.2 | 0 | 4.5 | 0 | 1.7 | 31.4 | 3.8 | 0 |

TABLE 10-D2

($CO_2$ free selectivities and $CO_2$ inclusive selectivity)- Pressure screening at a temperature of 380° C., GHSV of 4000 h$^{-1}$, and a $H_2$/CO ratio of 3

| | $CO_2$ free selectivities | | | | $CO_2$ inclusive selectivities | | | | |
| --- | --- | --- | --- | --- | --- | --- | --- | --- | --- |
| P (bar/MPa) | $CH_4$ (wt %) | $C_2H_6 + C_3H_8$ (wt %) | $C_4H_{10}$ (wt %) | Oxygenates + olefins (wt %) | $CO_2$ (wt %) | $CH_4$ (wt %) | $C_2H_6 + C_3H_8$ (wt %) | $C_4H_{10}$ (wt %) | Oxygenates + olefin (wt %)s |
| 20/2.0 | 3 | 82 | 15 | 1 | 71 | 1 | 24 | 4 | 0 |
| 20/2.0 | 4 | 83 | 12 | 1 | 72 | 1 | 23 | 3 | 0 |
| 20/2.0 | 2 | 83 | 14 | 0 | 70 | 1 | 25 | 4 | 0 |
| 20/2.0 | 4 | 82 | 12 | 1 | 71 | 1 | 24 | 4 | 0 |
| 20/2.0 | 4 | 81 | 15 | 0 | 70 | 1 | 25 | 4 | 0 |
| 20/2.0 | 5 | 81 | 13 | 1 | 70 | 1 | 24 | 4 | 0 |
| 20/2.0 | 13 | 73 | 12 | 2 | 70 | 4 | 22 | 4 | 1 |
| 20/2.0 | 36 | 34 | 5 | 24 | 66 | 12 | 12 | 2 | 8 |
| 50/5.0 | 6 | 78 | 15 | 1 | 66 | 2 | 27 | 5 | 0 |
| 50/5.0 | 5 | 79 | 15 | 1 | 67 | 2 | 26 | 5 | 0 |
| 50/5.0 | 5 | 79 | 15 | 1 | 65 | 2 | 28 | 5 | 0 |
| 50/5.0 | 5 | 79 | 15 | 1 | 66 | 2 | 27 | 5 | 0 |
| 50/5.0 | 7 | 77 | 15 | 1 | 64 | 3 | 27 | 5 | 0 |
| 50/5.0 | 22 | 12 | 2 | 65 | 54 | 10 | 5 | 1 | 30 |

TABLE 10-E1

GHSV screening at a temperature of 380° C., a pressure of 50 bar (5.0 MPa), a $H_2$/CO ratio of 3 and a catalyst wt ratio of HiFUEL R120/SAPO-34 of 3

| GHSV ($h^{-1}$) | TOS (hr) | CO CONV (mol %) | $C_1$ Sel (mol %) | | $C_2$ Sel (mol %) | | $C_3$ Sel (mol %) | | $C_4$ Sel (mol %) | | Oxygenates Sel (mol %) | | Other (mol %) |
| --- | --- | --- | --- | --- | --- | --- | --- | --- | --- | --- | --- | --- | --- |
| | | | $CO_2$ | $CH_4$ | $C_2H_4$ | $C_2H_6$ | $C_3H_6$ | $C_3H_8$ | $C_4H_8$ | $C_4H_{10}$ | DME | MeOH | |
| 4000 | 10 | 81.4 | 35.1 | 2.7 | 0 | 16 | 0 | 28.7 | 0 | 8.6 | 0 | 0.2 | 8.7 |
| 4000 | 50 | 79.4 | 36.5 | 2.6 | 0 | 15.6 | 0 | 29.7 | 0 | 8.8 | 0 | 0.2 | 6.8 |
| 10000 | 10 | 70.4 | 36.1 | 2.5 | 0 | 14.6 | 0.1 | 26.9 | 0 | 8 | 0.1 | 0.3 | 11.5 |
| 10000 | 50 | 36.5 | 40.5 | 3.9 | 0 | 12.6 | 0 | 23.4 | 0 | 6.6 | 4.4 | 2.6 | 6.0 |
| 13400 | 10 | 46.7 | 39.2 | 2.8 | 0 | 13.9 | 0 | 26.1 | 0 | 7.6 | 0.4 | 1.2 | 8.8 |
| 13400 | 50 | 13.1 | 34.4 | 11.9 | 0 | 6.9 | 0.3 | 8.9 | 0 | 2.3 | 26.9 | 8.4 | |

TABLE 10-E2

$CO_2$ free selectivities and $CO_2$ inclusive selectivity) - GHSV screening at a temperature of 380° C., a pressure of 50 bar (5000 kPa), a $H_2$/CO ratio of 3 and a catalyst wt ratio of HiFUEL R120/SAPO-34 of 3

| | $CO_2$ free selectivities | | | | $CO_2$ inclusive selectivities | | | | |
| --- | --- | --- | --- | --- | --- | --- | --- | --- | --- |
| GHSV ($h^{-1}$) | (wt %) $CH_4$ | (wt %) $C_2H_6 + C_3H_8$ | (wt %) $C_4H_{10}$ | (wt %) Oxygenates + olefins | (wt %) $CO_2$ | (wt %) $CH_4$ | (wt %) $C_2H_6 + C_3H_8$ | (wt %) $C_4H_{10}$ | (wt %) Oxygenates + olefins |
| 4000 | 5 | 79 | 15 | 1 | 65 | 2 | 28 | 5 | 0 |
| 4000 | 5 | 79 | 15 | 1 | 66 | 2 | 27 | 5 | 0 |
| 10000 | 5 | 78 | 15 | 2 | 67 | 2 | 26 | 5 | 1 |
| 10000 | 7 | 61 | 11 | 21 | 67 | 2 | 20 | 4 | 7 |
| 13400 | 6 | 74 | 14 | 6 | 68 | 2 | 23 | 4 | 2 |
| 13,400 | 14 | 17 | 3 | 66 | 53 | 7 | 8 | 1 | 31 |

TABLE 10-F1

$CO_2$ co-feed screening at a temperature of 380° C., a pressure of 40 bar (4.0 MPa), a $H_2$/CO volume ratio of 3, a GHSV of 3,800 h−1, and a catalyst wt ratio of HiFUEL R120/SAPO-34 of 3

| $CO_2$ in feed (vol %) | TOS (hr) | CO CONV (mol %) | $C_1$ Sel (mol %) | | $C_2$ Sel (mol %) | | $C_3$ Sel (mol %) | | $C_4$ Sel (mol %) | | Oxygenates Sel (mol %) | | Other (mol %) |
| --- | --- | --- | --- | --- | --- | --- | --- | --- | --- | --- | --- | --- | --- |
| | | | $CO_2$ | $CH_4$ | $C_2H_4$ | $C_2H_6$ | $C_3H_6$ | $C_3H_8$ | $C_4H_8$ | $C_4H_{10}$ | DME | MeOH | |
| 0 | 0 | 71.7 | 42.9 | 2.3 | 0 | 14.2 | 0 | 26.4 | 0 | 7.3 | 0 | 0.1 | 6.8 |
| 10 | 0 | 58.2 | 27 | 2 | 0 | 18.4 | 0 | 33.1 | 0 | 9.8 | 0 | 0.2 | 9.5 |
| 20 | 0 | 46 | 13.6 | 2 | 0 | 22.2 | 0 | 38.4 | 0 | 11.7 | 0 | 0.2 | 11.9 |

TABLE 10-F2

(CO$_2$ free selectivities and CO$_2$ inclusive selectivity)- CO$_2$ co-feed screening at a temperature of 380° C., a pressure of 40 bar (4000 kPa), a H$_2$/CO volume ratio of 3, a GHSV of 3,800 hr−1 and a catalyst wt ratio of HiFUEL R120/SAPO-34 of 3

| | CO$_2$ free selectivities | | | | CO$_2$ inclusive selectivities | | | | |
|---|---|---|---|---|---|---|---|---|---|
| CO$_2$ in feed (vol %) | (wt-%) CH$_4$ | (wt-%) C$_2$H$_6$ + C$_3$H$_8$ | (wt-%) C$_4$H$_{10}$ | (wt %) Oxygenates + olefins | (wt %) CO$_2$ | (wt %) CH$_4$ | (wt %) C$_2$H$_6$ + C$_3$H$_8$ | (wt %) C$_4$H$_{10}$ | (wt %) Oxygenates + olefins |
| 0 | 5 | 80 | 14 | 0 | 72 | 1 | 23 | 4 | 0 |
| 10 | 3 | 81 | 15 | 1 | 56 | 2 | 36 | 7 | 0 |
| 20 | 3 | 81 | 15 | 1 | 35 | 2 | 53 | 10 | 0 |

The data presented in Tables 10-A through 10-F demonstrate first, that in certain embodiments the invention may lead to production of a combination of saturated and unsaturated two carbon atom and three carbon atom hydrocarbons selected from ethane, ethylene, propane and propylene. Operating outside the parameters of the present invention may lead to production of oxygenates at temperatures below 350° C. at long TOS (see Table 10-A1 comparative data). Second, an increase in pressure within the ranges shown in the Examples leads to an increase in CO conversion. For example, Table 10-B shows that, at 20 bar (2.0 MPa) and higher, there is more than ten times the conversion that occurs at 5 bar (0.5 MPa), while at higher pressure, such as 35 bar (3.5 MPa), catalyst performance improves with TOS. Third, a certain minimum H$_2$:CO ratio is desirable for long term performance, with higher H$_2$:CO ratios tending to favor a reduction in CO$_2$ selectivity as shown in Table 10-C, where better catalyst stability is observed with a H$_2$:CO ratio of 3 or higher. Table 10-D also shows that, at a catalyst ratio (HiFUEL™ R120/SAPO-34) of 3 or less, better catalyst stability and productivity are observed. Fourth, within certain limits, higher GHSV rates may lead to faster catalyst deactivation than lower GHSV rates. For example, Table 10-E shows that, at a GHSV below 10000 h$^{-1}$, the catalyst performance is observed to be more stable than at higher GHSV. Fifth, use of a CO$_2$ co-feed may lead to a reduction in net CO$_2$ selectivity, as shown in Table 4-F1, where net CO$_2$ selectivity drops from 42.9% to 13.6% when the amount of CO$_2$ in the feedstream increases from 0 volume percent (vol %) to 20 vol %.

EXAMPLE 7

Physically mix 1 gram (g) of a copper-zinc-aluminum mixed metal oxide catalyst, having a copper (Cu) content of 39 wt %, a zinc (Zn) content of 25 wt %, and an aluminum content of 10 wt % (HiFUEL™ R120), with 0.33 gram of a silicoaluminophosphate catalyst (SAPO-34) by shaking them together in a bottle. Each of the catalysts has a particle size before mixing within a range of from 40 mesh (0.422 mm) to 80 mesh (0.178 mm). Activate the physically mixed catalyst using a pure hydrogen stream at a flow of 100 milliliters per minute (mL/min), a temperature of 270° C. and a pressure of 10 bar (1.0 MPa) for a period of 6 hours. Pressurize the system with pure nitrogen (N$_2$) up to 40 bar (4.0 MPa). Heat up the system to 400° C. while still flowing pure nitrogen. Pass 22.5 mL/min CO$_2$, 67.5 mL/min H$_2$ and 10 mL/min N$_2$ over the activated catalyst. Hold the temperature for 24 hours. Next, reduce the temperature by 25° C. and hold again for 24 hr. Repeat until a temperature of 300° C. is obtained. The results are recorded in Table 11.

The catalyst is loaded only once, prior to Run 1, for Runs 1-5, and no reloading is done. All conditions of pressure, W/F and H$_2$:CO$_2$ ratios are consistent for these runs, with only the temperature changed. New catalyst is loaded for each of Runs 6-14, and pressure, W/F, H$_2$:CO$_2$ ratio, or MMO/SAPO-34 weight ratios are changed as shown in Table 12. This Example 6 shows that, despite the changes in parameters, a product mixture falling within the definition of claim 1 can be obtained, although the exact amounts of C1, C2 and C3 products are somewhat altered. Runs 9, 10 and 14 in Table 11 provide examples of optimized reaction conditions resulting in higher production of C2 and C3 paraffins.

TABLE 11

Screening data from Example 7 for CuO/ZnO/Al$_2$O$_3$ + SAPO-34 catalyst and CO$_2$ + H$_2$ feed with varying temperatures, pressures, H$_2$/CO$_2$ ratios, W/F, and MMO/SAPO ratios.

| | | | | W/F | MMO | | | | CO— and CO2— free, carbon based selectivities | | |
|---|---|---|---|---|---|---|---|---|---|---|---|
| Run | T ° C. | P (bar) | H$_2$:CO$_2$ ratio | (g-cat * h/-mol) | cat/-SAPO (wt/wt) | H2 CONV (%) | CO2 CONV (%) | COx CONV (%) | Methane (%) | C2 (%) | C2= (%) |
| 1 | 400 | 40 | 3 | 5.5 | 3.0 | 14.5 | 37 | 1.6 | 22 | 30 | 0 |
| 2 | 375 | 40 | 3 | 5.5 | 3.0 | 16.5 | 33.8 | 5.3 | 6 | 26 | 0 |
| 3 | 350 | 40 | 3 | 5.5 | 3.0 | 17.8 | 30.7 | 7.9 | 5 | 22 | 0 |
| 4 | 325 | 40 | 3 | 5.5 | 3.0 | 14.3 | 27.3 | 3.7 | 7 | 12 | 0 |
| 5 | 300 | 40 | 3 | 5.5 | 3.0 | 11.1 | 23.4 | 2.9 | 0 | 0 | 0 |
| 6 | 350 | 28 | 3 | 5.5 | 3.0 | 11.7 | 30.5 | 1.6 | 7 | 25 | 0 |
| 7 | 350 | 2 | 3 | 5.5 | 3.0 | 10.4 | 28.7 | 0 | 0 | 0 | 0 |
| 8 | 350 | 40 | 1 | 5.5 | 3.0 | 21.5 | 18.7 | 1.5 | 4 | 25 | 0 |
| 9 | 350 | 40 | 10 | 5.5 | 3.0 | 11.5 | 51.5 | 24.7 | 7 | 22 | 0 |
| 10 | 350 | 40 | 3 | 19.6 | 3.0 | 11.7 | 51.2 | 24.4 | 7 | 22 | 0 |
| 11 | 350 | 40 | 3 | 1 | 3.0 | 13.5 | 30.5 | 1.3 | 0 | 16 | 0 |

TABLE 11-continued

Screening data from Example 7 for CuO/ZnO/Al$_2$O$_3$ + SAPO-34 catalyst and CO$_2$ + H$_2$ feed with varying temperatures, pressures, H$_2$/CO$_2$ ratios, W/F, and MMO/SAPO ratios.

| 12 | 350 | 40 | 3  | 5.5  | 10  | 14.8 | 29.6 | 4.4  | 5  | 23 | 0 |
| 13 | 350 | 40 | 3  | 5.5  | 0.1 | 16.8 | 29.9 | 6.7  | 4  | 22 | 0 |
| 14 | 350 | 40 | 10 | 19.6 | 3.0 | 12.9 | 53.1 | 29.4 | 11 | 21 | 0 |

| | CO— and CO2— free, carbon based selectivities | | | | | | | | C2 + C3 paraffin yield (%) | C1 yield (%) |
|---|---|---|---|---|---|---|---|---|---|---|
| Run | C3 (%) | C3= (%) | C4 (%) | C4= (%) | C5 (%) | C5= (%) | MeOH (%) | DME (%) | | |
| 1  | 35 | 0 | 9  | 0 | 0 | 0 | 3  | 1  | 1.0  | 0.4 |
| 2  | 47 | 0 | 14 | 0 | 4 | 0 | 2  | 1  | 3.8  | 0.3 |
| 3  | 48 | 0 | 15 | 0 | 6 | 0 | 2  | 1  | 5.6  | 0.4 |
| 4  | 27 | 0 | 8  | 0 | 0 | 0 | 19 | 27 | 1.4  | 0.3 |
| 5  | 1  | 0 | 0  | 0 | 0 | 0 | 57 | 42 | 0.0  | 0.0 |
| 6  | 51 | 0 | 0  | 0 | 0 | 0 | 10 | 4  | 1.2  | 0.1 |
| 7  | 0  | 0 | 3  | 0 | 0 | 0 | 0  | 0  | 0.0  | 0.0 |
| 8  | 48 | 0 | 0  | 0 | 4 | 0 | 3  | 2  | 1.1  | 0.1 |
| 9  | 49 | 0 | 14 | 0 | 5 | 0 | 1  | 1  | 17.6 | 1.8 |
| 10 | 49 | 0 | 14 | 0 | 5 | 0 | 1  | 1  | 17.3 | 1.7 |
| 11 | 34 | 0 | 15 | 0 | 1 | 0 | 19 | 20 | 0.7  | 0.0 |
| 12 | 46 | 0 | 10 | 0 | 5 | 0 | 4  | 3  | 3.0  | 0.2 |
| 13 | 55 | 0 | 14 | 0 | 3 | 0 | 1  | 0  | 5.1  | 0.3 |
| 14 | 45 | 0 | 15 | 0 | 5 | 0 | 1  | 1  | 19.4 | 3.2 |

The extent of reaction is calculated as COx conversion, where the reaction of CO$_2$ into CO does not contribute to the conversion calculation.

TABLE 12

Screening data from Example 7 reported as wt % of outlet, excluding CO, CO$_2$ and H$_2$.

| | Wt % of outlet, excluding CO, CO$_2$ and H2 | | | | | | | | | |
|---|---|---|---|---|---|---|---|---|---|---|
| Run | Methane (%) | C2 (%) | C2= (%) | C3 (%) | C3= (%) | C4 (%) | C4= (%) | C5 (%) | C5= (%) | MeOH (%) | DME (%) |
| 1  | 22.9 | 28.9 | 0.0 | 32.8 | 0.0 | 8.1  | 0.0 | 0.0 | 0.0 | 6.0  | 1.4  |
| 2  | 6.3  | 25.6 | 0.0 | 45.4 | 0.0 | 13.6 | 0.0 | 3.8 | 0.0 | 4.2  | 1.1  |
| 3  | 5.0  | 22.0 | 0.0 | 46.6 | 0.0 | 14.2 | 0.0 | 5.5 | 0.0 | 5.7  | 2.1  |
| 4  | 5.7  | 9.1  | 0.0 | 19.1 | 0.0 | 5.6  | 0.0 | 0.0 | 0.0 | 29.5 | 30.9 |
| 5  | 0.0  | 0.0  | 0.0 | 0.6  | 0.0 | 0.0  | 0.0 | 0.0 | 0.0 | 65.4 | 34.0 |
| 6  | 6.6  | 22.2 | 0.0 | 44.2 | 0.0 | 2.6  | 0.0 | 0.0 | 0.0 | 18.9 | 5.4  |
| 7  | 4.4  | 24.7 | 0.0 | 46.2 | 0.0 | 12.9 | 0.0 | 3.9 | 0.0 | 5.5  | 2.4  |
| 8  | 7.6  | 22.4 | 0.0 | 47.7 | 0.0 | 13.8 | 0.0 | 4.9 | 0.0 | 2.2  | 1.6  |
| 9  | 7.4  | 21.9 | 0.0 | 47.7 | 0.0 | 14.5 | 0.0 | 4.8 | 0.0 | 2.1  | 1.5  |
| 10 | 0.0  | 12.2 | 0.0 | 25.4 | 0.0 | 7.4  | 0.0 | 0.7 | 0.0 | 30.9 | 23.4 |
| 11 | 5.1  | 21.4 | 0.0 | 42.6 | 0.0 | 13.0 | 0.0 | 4.6 | 0.0 | 8.5  | 4.9  |
| 12 | 4.4  | 21.7 | 0.0 | 53.6 | 0.0 | 15.0 | 0.0 | 3.0 | 0.0 | 2.2  | 0.0  |
| 13 | 12.0 | 21.5 | 0.0 | 45.0 | 0.0 | 12.9 | 0.0 | 4.9 | 0.0 | 2.2  | 1.6  |
| 14 | 37.5 | 39.3 | 0.0 | 20.2 | 0.0 | 3.0  | 0.0 | 0.0 | 0.0 | 0.0  | 0.0  |

As noted in Table 11, the extent of reaction is calculated as COx conversion, where the reaction of CO$_2$ into CO does not contribute to the conversion calculation.

COMPARATIVE EXAMPLE C

Two embodiments of the inventive catalyst system are tested against a catalyst system as described in Park, Y.-K.; Park, K.-C.; Ihm, S.-K., "Hydrocarbon synthesis through CO$_2$ hydrogenation over CuZnOZrO$_2$/zeolite hybrid catalysts," *Catalysis Today* 44 (1998) 165-173, hereinafter "Park," in a hydrogenation of CO$_2$. Two separate mixed catalyst beds made up of the components for each catalyst, as shown in Table 13, are prepared, wherein the weight ratio of the mixed metal oxide to the zeolite component is 1:1. A mixed flow of hydrogen and carbon dioxide, in a H$_2$:CO$_2$ volumetric ratio of 3:1, is flowed through each catalyst bed at a pressure of 28 bar (2.8 MPa); a temperature of 400° C.; and a catalyst g per flow rate of 20 g-cat·h/mol. Products produced and weight percentages thereof, based upon 100 weight percent, are shown in Table 13.

TABLE 13

CO$_2$ hydrogenation over hybrid catalysts, Park data only.

| | Hybrid Catalyst | |
|---|---|---|
| | CuZnOZrO$_2$ + H-ZSM-5* | CuZnOZrO$_2$ + SAPO-34* |
| CO$_2$ conversion (%) | 38.4 | 33.9 |
| Yield (%): | | |
| HC   | 2.7  | 12.2 |
| CO   | 34.7 | 20.5 |
| MeOH | 1.0  | 1.2  |
| DME  | 0.0  | 0.0  |

TABLE 13-continued

CO$_2$ hydrogenation over hybrid catalysts, Park data only.

| | Hybrid Catalyst | |
|---|---|---|
| | CuZnOZrO$_2$ + H-ZSM-5* | CuZnOZrO$_2$ + SAPO-34* |
| HC selectivity (wt %) | | |
| C$_1$ | 17.5 | 2.1 |
| C$_2$ | 75.4 | 34.2 |
| C$_3$ | 5.5 | 53.1 |
| C$_4$ | 1.2 | 9.6 |
| C$_5$ | 0.4 | 0.8 |
| C$_6^+$ | 0.0 | 0.2 |
| C$_2^+$ yield | 2.2 | 11.9 |

*Park catalyst

Table 13 shows that, for the Park process, yield of C$_2$ and C$_3$ hydrocarbons is 10.7 wt % ((34.2+53.1)/100·12.2 wt %=10.7 wt %), and yield of CH$_4$ is 0.3 wt % (2.1/100·12.2 wt %=0.3 wt %).

The Park data is then employed to compare the inventive catalyst system with the Park catalyst system, under the conditions employed in Park, including temperature (400° C.), pressure (28 bar, 2.8 MPa), weight catalyst per flow rate (W/F) of 20 g-cat*h/mol, H$_2$:CO$_2$ volumetric ratio of 3, and a mixed metal oxide catalyst to molecular sieve catalyst ratio of 1:1 on a weight/weight basis. Results are shown in Table 14.

TABLE 14

Comparison of yields using Park and Example catalysts under Park conditions.

| Hybrid catalyst | C2 + C3 hydrocarbon yield | C1 hydrocarbon yield |
|---|---|---|
| CuZnOZrO$_2$ + SAPO-34* | 10.7 | 0.3 |
| CuO/ZnO/Al$_2$O$_3$ + SAPO-34** | 0.8 | 0.5 |
| Cr$_2$O$_3$/ZnO + SAPO-34** | 5.4 | 5.4 |

*Park catalyst
**Example catalyst.

EXAMPLE 8

A mixed catalyst comprising CuO/ZnO/Al$_2$O$_3$ is employed in a reaction to show the alteration in yields, and improvement in C$_2$ and C$_3$ yield, attributable to use of conditions including a temperature of 350° C., a pressure of 40 bar (4 MPa), a weight to flow ratio (W/F) of 19.6 g-cat*h/mol, a H$_2$:CO$_2$ ratio of 10:1, and a mixed metal oxide catalyst to weight/weight ratio of 3:1. Results are shown in Table 15.

TABLE 15

Hydrocarbon yields at given conditions.

| Hybrid catalyst | C2 + C3 hydrocarbon yield | C1 hydrocarbon yield |
|---|---|---|
| CuO/ZnO/Al$_2$O$_3$ + SAPO-34** | 19.4 | 3.2 |

**Example catalyst

This Example 8 shows that the example catalyst under the given claimed process conditions shows better performance than the Park catalyst under Park's conditions.

EXAMPLE 9

A Cr$_2$O$_3$/ZnO catalyst is prepared as follows:

A 0.14 molar (M) cation solution is prepared via addition of appropriate quantities (targeting a Cr to Zn molar ratio of 0.4:1) of Cr(NO$_3$)$_3$·9H$_2$O and Zn(NO$_3$)$_2$·3H$_2$O to distilled water (H$_2$O). In addition, a 0.5 M solution of (NH$_4$)$_2$CO$_3$ is prepared as a precipitating agent. The cation (Cr$_3^+$/Zn$_2^+$) and anion ((CO$_3$)$_2$) solutions are simultaneously added dropwise to a stirred beaker of distilled H$_2$O maintained at 7.0<=pH<=7.5 and T=338+/−5 K. Co-precipitated materials are filtered, washed repeatedly with distilled water, dried in static air at 383 K, and subsequently calcined at 873 K for 2 hr.

The prepared Cr$_2$O$_3$/ZnO catalyst is then physically mixed with a silicoaluminophosphate catalyst (SAPO-34) by taking appropriate amounts to reach the weight ratio as indicated in Table 16 hereinbelow and shaking them together in a bottle. Each of the catalysts has a particle size before mixing within a range of from 40 mesh (0.422 mm) to 80 mesh (0.178 mm). Pressurize the system with pure N$_2$ up to the value as indicated in Table 15. Heat up the system to the value as indicated in Table 16 while still flowing pure N$_2$. Switch off the flow of nitrogen and start passing a certain amount of CO, H$_2$ and He over the catalyst to reach the feed ratio and GHSV as indicated in the table. The results are shown in Table 16.

TABLE 16

Screening of Cr$_2$O$_3$/ZnO + SAPO-34 catalyst at varying pressures, cat ratios, and GHSVs.

| | | | | | | Wt % of outlet, excluding CO, CO$_2$ and H$_2$ | | |
|---|---|---|---|---|---|---|---|---|
| T (° C.) | P (bar/-MPa) | Cat ratio (wt/wt) | GHSV (h$^{-1}$) | H$_2$:CO ratio (v/v) | TOS (hr) | CO CONV (mol %) | Methane (wt %) | C2 (wt %) | C2= (wt %) |
| 400 | 50/5.0 | 2 | 2000 | 3 | 10 | 67.0 | 12.5 | 11.7 | 1.6 |
| 400 | 50/5.0 | 2 | 2000 | 3 | 50 | 63.6 | 14.4 | 13.5 | 0.0 |
| 400 | 70/7.0 | 2 | 1000 | 3 | 10 | 81.6 | 13.9 | 23.6 | 0.0 |
| 400 | 70/7.0 | 2 | 1000 | 3 | 50 | 78.7 | 14.7 | 22.0 | 0.0 |
| 400 | 50/5.0 | 1 | 1000 | 3 | 10 | 74.2 | 14.8 | 27.0 | 0.0 |
| 400 | 50/5.0 | 1 | 1000 | 3 | 50 | 71.1 | 10.6 | 23.1 | 0.0 |

TABLE 16-continued

Screening of $Cr_2O_3/ZnO$ + SAPO-34 catalyst at varying pressures, cat ratios, and GHSVs.

| | Wt % of outlet, excluding CO, $CO_2$ | | | | | | | |
|---|---|---|---|---|---|---|---|---|
| T (° C.) | C3 (wt %) | C3= (wt %) | C4 (wt %) | C4= (wt %) | C5 (wt %) | C5= (wt %) | MeOH (wt %) | DME (wt %) |
| 400 | 57.3 | 1.6 | 12.9 | 0.0 | 2.4 | 0.0 | 0.0 | 0.0 |
| 400 | 57.6 | 1.6 | 11.4 | 0.0 | 1.6 | 0.0 | 0.0 | 0.0 |
| 400 | 48.5 | 1.1 | 10.6 | 0.0 | 1.5 | 0.0 | 0.0 | 0.8 |
| 400 | 49.5 | 1.0 | 10.3 | 0.0 | 1.7 | 0.0 | 0.0 | 0.8 |
| 400 | 45.3 | 0.6 | 10.0 | 0.0 | 1.0 | 0.0 | 0.0 | 1.3 |
| 400 | 52.2 | 0.7 | 11.3 | 0.0 | 1.0 | 0.0 | 0.0 | 1.0 |

EXAMPLE 10

Replicate Example 6, but change the catalyst type in a first run to a mixture $CuO/ZnO/Al_2O_3$ and a combination of molecular sieve catalysts comprised of 75 wt % SAPO-5 and 25 wt % of SAPO-34.

In a second run, change the catalyst type to a mixture of $CuO/ZnO/Al_2O_3$ and SAPO-18.

For a third run, physically mix 50 microliters (4) of a $CuO/ZnO/Al_2O_3$ mixed metal oxide catalyst that has a Cu content of 39 wt %, a Zn content of 25 wt %, and an Al content of 10 wt % (HiFUEL™ R120) with 150 μL of a H-Beta zeolite (ZEOCAT™ PB/H, $SiO_2/Al_2O_3$ ratio=24, available from Zeochem AG, Switzerland) by shaking them together in a bottle.

Each of the catalysts has a particle size before mixing ranging from 40 mesh (0.422 mm) to 80 mesh (0.178 mm). For the first and second run, activate the physically mixed catalyst according to Example 6. For the third run, activate the physically mixed catalyst using a mix of $H_2$ and He at a 90:10 vol %/vol % ratio, at a GHSV of 2400 $h^{-1}$, a temperature of 300° C. and a pressure of 3 bar (0.3 MPa) for a period of 6 hr.

Pass a mixture of $H_2$ and CO, volumetric ratio $H_2$:CO=3, over each activated catalyst under the conditions shown in Table 17. Table 18 illustrates the corresponding wt % of outlet, excluding $CO_2$, CO and $H_2$, for each of the three catalyst runs.

TABLE 17

Comparison of different molecular sieve catalysts in conversion of CO.

| Catalyst | P (bar-/MPa) | H2:CO ratio (v/v) | GHSV (hr–1) | MMO/-zeollite ratio (wt/wt) | T (° C.) | CO CONV | Carbon based selectivities | | |
|---|---|---|---|---|---|---|---|---|---|
| | | | | | | | CH4 (%) | C2H4 (%) | C2H6 (%) |
| CuO/ZnO/-Al2O3 + (75 wt % SAPO-5 + 25 wt % SAPO-34) | 50/5.0 | 3 | 4000 | 3 | 380 | 79.2 | 2.5 | 0.0 | 15.0 |
| CuO/ZnO/-Al2O3 + SAPO-18 | 50/5.0 | 3 | 4000 | 3 | 400 | 69.0 | 4.9 | 0.0 | 14.9 |
| CuO/ZnO/-Al2O3 + Beta | 30/3.0 | 3 | 1950 | 0.6 | 385 | 70.5 | 6.2 | 0.0 | 14.4 |

| Catalyst | Carbon based selectivities | | | | | | | | |
|---|---|---|---|---|---|---|---|---|---|
| | C3H6 (%) | C3H8 (%) | C4H8 (%) | C4H10 (%) | C5H10 (%) | C5H12 (%) | MeOH | DME | $CO_2$ |
| CuO/ZnO/-Al2O3 + (75 wt % SAPO-5 + 25 wt % SAPO-34) | 0.0 | 29.9 | 0.0 | 8.8 | 0.0 | 2.8 | 0.1 | 3.6 | 37.3 |
| CuO/ZnO/-Al2O3 + SAPO-18 | 0.0 | 33.2 | 0.0 | 7.6 | 0.0 | 1.6 | 0.1 | 0.0 | 37.8 |
| CuO/ZnO/-Al2O3 + Beta | 0.0 | 24.5 | 0.0 | 6.1 | 0.0 | 0.9 | 0.0 | 0.0 | 47.9 |

TABLE 18

Wt % of outlet corresponding to use of different molecular sieve catalysts.

| | Wt % of outlet, excluding $CO_2$, CO and $H_2$ | | | | | | | | | | |
|---|---|---|---|---|---|---|---|---|---|---|---|
| Catalyst | CH4 (wt %) | C2H4 (wt %) | C2H6 (wt %) | C3H6 (wt %) | C3H8 (wt %) | C4H8 (wt %) | C4H10 (wt %) | C5H10 (wt %) | C5H12 (wt %) | MeOH (wt %) | DME (wt %) |
| CuO/ZnO/Al2O3 + (75 wt % SAPO-5 + 25 wt % SAPO-34 | 4.2 | 0.0 | 23.5 | 0.0 | 45.8 | 0.0 | 13.4 | 0.0 | 4.3 | 0.4 | 8.6 |
| CuO/ZnO/Al2O3 + SAPO-18 | 8.5 | 0.0 | 24.2 | 0.0 | 52.7 | 0.0 | 11.9 | 0.0 | 2.4 | 0.4 | 0.0 |
| CuO/ZnO/Al2O3 + Beta | 12.9 | 0.0 | 27.8 | 0.0 | 46.3 | 0.0 | 11.4 | 0.0 | 1.7 | 0.0 | 0.0 |

The invention claimed is:

1. A process for preparing $C_2$ and $C_3$ hydrocarbons comprising
   (a) introducing a feedstream into a reactor, the feedstream comprising hydrogen gas and a gas selected from carbon monoxide, carbon dioxide, and combinations thereof, such that the hydrogen gas is present in an amount of from 10 volume percent to 90 volume percent, based on combined volumes of the hydrogen gas and the gas selected from carbon monoxide, carbon dioxide, and combinations thereof; and
   (b) contacting the feedstream and a mixed catalyst in the reactor, the mixed catalyst comprising as components
      (1) a mixed metal oxide catalyst selected from
         a copper oxide catalyst,
         a copper oxide/zinc oxide catalyst,
         a copper oxide/alumina catalyst,
         a copper oxide/zinc oxide/alumina catalyst,
         a chromium oxide/zinc oxide catalyst, and
         combinations thereof; and
      (2) a non-metal-modified molecular sieve catalyst selected from SAPO-34, SSZ-13, SAPO-18, SAPO-5, SAPO-11, Beta-zeolite, ZSM-58, and combinations thereof, such names corresponding to the naming convention of the International Zeolite Association;
   under reaction conditions sufficient to form a product mixture, the reaction conditions comprising
      a reactor temperature ranging from 300 degrees Celsius to 440 degrees Celsius;
      a pressure of at least one bar (100 kilopascals); and
      a gas hourly space velocity of at least 500 reciprocal hours;
   the product mixture having, as calculated on a carbon monoxide-free, carbon dioxide-free, and hydrogen-free basis,
      a combined ethane and propane content that is more than 45 percent by weight;
      a methane content of less than 15 percent by weight;
      a combined butane and higher saturated hydrocarbon content of less than 30 percent by weight; and
      a combined unsaturated hydrocarbon and oxygenate content of less than 10 percent by weight;
   each weight percentage being based upon total product mixture weight and, when taken together, equaling 100 percent by weight.

2. The process of claim 1 wherein
   the feedstream comprises carbon in the form of carbon monoxide in an amount greater than 50 mole percent, based on total carbon in the feedstream, such that
      the volumetric ratio of hydrogen gas to carbon monoxide ranges from 0.1:1 to 10:1;
      the mixed metal oxide catalyst is a copper oxide/zinc oxide/alumina catalyst; and
      the molecular sieve catalyst is SAPO-34.

3. The process of claim 1 wherein
   the feedstream comprises carbon in the form of carbon monoxide in an amount greater than 50 mole percent, based on total carbon in the feedstream, such that
      the volumetric ratio of hydrogen gas to carbon monoxide ranges from 0.1:1 to 10:1;
      the mixed metal oxide catalyst is a chromium oxide/zinc oxide catalyst; and
      the molecular sieve catalyst is SAPO-34.

4. The process of claim 1 wherein the temperature ranges from 350° C. to 440° C.;
   the pressure is at least 20 bar (2.0 megapascals); and
   the gas hourly space velocity ranges from 500 reciprocal hours to 12000 reciprocal hours.

5. The process of claim 1 wherein
   the feedstream comprises carbon in the form of carbon dioxide in an amount greater than 50 mole percent, based on total carbon in the feedstream, such that
      the volumetric ratio of hydrogen gas to carbon dioxide ranges from 0.1:1 to 10:1;
      the mixed metal oxide catalyst is a copper oxide/zinc oxide/alumina catalyst; and
      the molecular sieve catalyst is SAPO-34.

6. The process of claim 1 wherein
   the feedstream comprises carbon in the form of carbon dioxide in an amount greater than 50 mole percent, based on total carbon in the feedstream, such that
      the volumetric ratio of hydrogen gas to carbon dioxide ranges from 0.1:1 to 10:1;
      the mixed metal oxide catalyst is a chromium oxide/zinc oxide catalyst; and
      the molecular sieve catalyst is SAPO-34.

7. The process of claim 5 wherein
   the temperature ranges from 300° C. to 400° C.;
   the pressure is at least 2 bar (0.2 megapascals); and
   the gas hourly space velocity ranges from 500 reciprocal hours to 22000 reciprocal hours.

8. The process of claim 1 wherein
   the mixed catalyst has a weight/weight ratio of mixed metal oxide catalyst to molecular sieve ranging from 0.1:1 to 10:1.

9. The process of claim 1 wherein
   the product mixture has, as calculated on a carbon monoxide-free, carbon dioxide-free, and hydrogen-free basis,
      a combined ethane and propane content of more than 60 percent by weight;
      a methane content of less than 10 percent by weight;
      a combined butane and higher saturated hydrocarbon content of less than 25 percent by weight; and a combined unsaturated hydrocarbon and oxygenate content of less than 5 percent by weight;

each weight percentage being based upon total product mixture weight and, when taken together, equaling 100 weight percent.

10. The process of claim 1, wherein the mixed catalyst consists essentially of
  (1) a mixed metal oxide catalyst selected from
    a copper oxide catalyst,
    a copper oxide/zinc oxide catalyst,
    a copper oxide/alumina catalyst,
    a copper oxide/zinc oxide/alumina catalyst,
    a chromium oxide/zinc oxide catalyst, and
    combinations thereof; and
  (2) a non-metal-modified molecular sieve catalyst selected from SAPO-34, SSZ-13, SAPO-18, SAPO-5, SAPO-11, Beta-zeolite, ZSM-58, and combinations thereof, such names corresponding to the naming convention of the International Zeolite Association.

\* \* \* \* \*